US008192951B2

(12) United States Patent
Wang et al.

(10) Patent No.: US 8,192,951 B2
(45) Date of Patent: Jun. 5, 2012

(54) GLYCOLYSIS-INHIBITING SUBSTANCES IN CELL CULTURE

(75) Inventors: Wenge Wang, Chelmsford, MA (US); Yen Tung Luan, Chelmsford, MA (US)

(73) Assignee: Wyeth LLC, Madison, NJ (US)

( * ) Notice: Subject to any disclaimer, the term of this patent is extended or adjusted under 35 U.S.C. 154(b) by 903 days.

(21) Appl. No.: 11/934,458

(22) Filed: Nov. 2, 2007

(65) Prior Publication Data

US 2008/0108106 A1 May 8, 2008

Related U.S. Application Data

(60) Provisional application No. 60/856,615, filed on Nov. 3, 2006.

(51) Int. Cl.
*C12P 21/00* (2006.01)
*C12N 5/00* (2006.01)

(52) U.S. Cl. .................. 435/69.1; 435/405; 435/404

(58) Field of Classification Search .................. None
See application file for complete search history.

(56) References Cited

U.S. PATENT DOCUMENTS

| 4,399,216 | A | 8/1983 | Axel et al. |
| 4,522,811 | A | 6/1985 | Eppstein et al. |
| 4,816,397 | A | 3/1989 | Boss et al. |
| 4,816,567 | A | 3/1989 | Cabilly et al. |
| 5,078,996 | A | 1/1992 | Conlon et al. |
| 5,166,320 | A | 11/1992 | Bloomfield et al. |
| 5,223,409 | A | 6/1993 | Ladner et al. |
| 5,225,539 | A | 7/1993 | Winter |
| 5,549,892 | A | 8/1996 | Friedman et al. |
| 5,585,089 | A | 12/1996 | Queen et al. |
| 5,693,761 | A | 12/1997 | Queen et al. |
| 5,693,762 | A | 12/1997 | Queen et al. |
| 5,859,205 | A | 1/1999 | Adair et al. |
| 6,300,064 | B1 | 10/2001 | Knappik et al. |
| 6,407,213 | B1 | 6/2002 | Carter et al. |
| 7,294,484 | B2 * | 11/2007 | Drapeau et al. ............ 435/69.1 |
| 7,300,773 | B2 * | 11/2007 | Drapeau et al. ............ 435/69.1 |
| 7,335,491 | B2 * | 2/2008 | Drapeau et al. ............ 435/69.1 |
| 2003/0070185 | A1 | 4/2003 | Jakobovits et al. |
| 2004/0082764 | A1 | 4/2004 | Kunz et al. |
| 2004/0142382 | A1 | 7/2004 | Veldman et al. |
| 2008/0081356 | A1 | 4/2008 | Lasko et al. |

FOREIGN PATENT DOCUMENTS

| EP | 117058 | 8/1984 |
| EP | 117060 | 8/1984 |
| EP | 171496 | 2/1986 |
| EP | 0173494 | 3/1986 |
| EP | 0239400 | 9/1987 |
| EP | 417563 | 3/1991 |
| EP | 418014 | 3/1991 |
| GB | 2177096 B | 3/1986 |
| WO | WO92/18619 | 0/1019 |
| WO | WO 90/02809 | 3/1990 |
| WO | WO91/11172 | 8/1991 |
| WO | WO 91/17271 | 11/1991 |
| WO | WO 92/01047 | 1/1992 |
| WO | WO92/06193 | 4/1992 |
| WO | WO 92/09690 | 6/1992 |
| WO | WO 92/13069 | 8/1992 |
| WO | WO 92/15679 | 9/1992 |
| WO | WO 92/20791 | 11/1992 |
| WO | WO 93/01288 | 1/1993 |
| WO | WO94/02518 | 2/1994 |
| WO | WO 96/33735 | 10/1996 |
| WO | WO 96/34096 | 10/1996 |
| WO | WO98/17799 | 4/1998 |
| WO | WO 98/20734 | 5/1998 |
| WO | WO 98/52976 | 11/1998 |
| WO | WO98/55148 | 12/1998 |
| WO | WO99/43839 | 9/1999 |
| WO | WO 00/18434 | 4/2000 |
| WO | WO 00/34317 | 6/2000 |
| WO | WO 02/98368 | 6/2002 |
| WO | WO 02/098368 | 12/2002 |
| WO | WO 02/098369 | 12/2002 |
| WO | WO 02/98369 | 12/2002 |

OTHER PUBLICATIONS

Malcolmn et al Characterization of iodoacetate-mediated neurotoxicity in vitro using primary cultures of rat cerebellar granule cells Free radical Biology and Medicine, 2000 vol. 28, No. 1, p. 102-107.*
Russle et al (Biodegradation of tributyl phosphate by naturally occurring microbial isolates and coupling to the removal of uranium from aqueous solution Environmental Science and technology 1996, 30, pp. 2371-2375.*
Luo et al., "Hypoxia-inducible transcription factor-1α promotes hypoxia-induced A549 apoptosis via a mechanism that involves the glycolysis pathway," BMC Cancer 6:26 (2006).
Downs et al., "Glucose utilization during gonadotropin-induced meiotic maturation in *cumulus* cell-enclosed mouse oocytes," *Molecular Reproduction and Development* 44(1):121-131 (1996).
Bergbauer et al., "Studies on fructose metabolism in cultured astroglial cells and control hepatocytes: lack of fructokinase activity and immunoreactivity in astrocytes," *Developmental Neuroscience* 18(5-6):371-379 (1996).
Basma et al., 1-Methyl-4-(2'-Ethylphenyl)-1,2,3,6-Tetrahydropyridine-Induced Toxicity in PC12 Cells is Enhanced by Preventing Glycolysis, Journal of Neurochemistry 58(3):1052-1059 (1992).
International Search Report, PCT/US2007/083473, date of mailing Nov. 20, 2008.
Written Opinion, PCT/US2007/083473, date of mailing Nov. 20, 2008.
Lemarchand et al. (1992) Proc. Natl. Acad. Sci. USA 89:6482-6486, "Adenovirus-mediated transfer of a recombinant human alpha1-antitrypsin cDNA to human endothelial cells".
Mansour et al. (1988) Nature 336:348-352, "Disruption of the proto-oncogene int-2 in mouse embryo-derived stem cells: a general strategy for targeting mutations to non-selectable genes".

(Continued)

*Primary Examiner* — Kagnew H Gebreyesus
(74) *Attorney, Agent, or Firm* — Pfizer Inc.

(57) ABSTRACT

An improved system for large scale production of proteins and/or polypeptides in cell culture is provided. In accordance with the present invention, cells expressing the protein or polypeptide of interest are grown in media that comprise a glycolysis-inhibiting substance. Additionally and/or alternatively, cells expressing the protein or polypeptide of interest are grown in media in which glutamine is limited. The use of such a system allows high levels of protein or polypeptide production and lessens accumulation of undesirable metabolic waste products such as lactate. Proteins and polypeptides expressed in accordance with the present invention may be advantageously used in the preparation of pharmaceutical, immunogenic, agricultural or other commercial compositions.

7 Claims, 7 Drawing Sheets

OTHER PUBLICATIONS

Mather et al. (1982) Annals N.Y. Acad. Sci. 383:44-68, "Culture of Testicular Cells in Hormone-Supplemented Serum-Free Medium".
Samulski et al. (1989) J. Virol. 63(9):3822-3828, "Helper-Free Stocks of Recombinant Adeno-Associated Viruses: Normal Integration Does Not Require Viral Gene Expression".
Schenk et al. (1999) Nature 400:173-177, "Immunization with amyloid-beta attenuates Alzheimer-disease-like pathology in the PDAPP mouse".
Bard et al. (2000) Nat. Med. 6:916-19, "Peripherally administered antibodies against amyloid beta peptide enter the central nervous system and reduce pathology in a mouse model of Alzheimer disease".
Berkner et al. (1988) BioTechniques 6:616, "Develpoment of Adenovirus Vectors for the Expression of Heterologous Genes".
Bird et al. (1988) Science 242:423-26, "Single-Chain Antigen-Binding Proteins".
Capel et al. (1994) Immunomethods 4:25-34, "Heterogeneity of Human IgG Fc Receptors".
Chang et al. (1997) J. Clin. Invest. 100:4, "Replacing the First Epidermal Growth Factor-like Domain of Factor IX with that of Factor VII Enhances Activity in Vitro and in Canine Hemophilia B".
Chartier Harlan et al. (1991) Nature 353:844, " Early-onset Alzheimer's disease caused by mutations at codon 717 of the β-amyloid precursor protein gene".
Chothia, D. et al. (1992) J. Mol. Biol. 227:799-817, "Structural Repertoire of the Human VH Segments".
Cook, G. P. et al. (1995) Immunol. Today 16 (5): 237-242, "The Human Immunoglobulin VH Repertoire".
Datta, R. et al. (1992) Proc. Natl. Acad. Sci. USA 89:10149-10153, "Ionizing radiation activates transcription of the EGR1 gene via CArG elements".
de Haas et al. (1995) J. Lab. Clin. Med. 126:330-41, "Fcγ receptors of phagocytes".
DeVries et al. (1992) Science 255; 989-991, "The fms-like Tyrosine Kinase, a receptor for vascular endothelial growth factor".
Dodel et al. (2003) Lancet Neurology 2:215, "Immunotherapy for Alzheimer's Disease".
Drews (1996) Nature Biotechnology, 14:1516, "Genomic sciences and the medicine of tomorrow".
Flotte et al. (1992) Am. J. Respir. Cell Mol. Biol. 7:349-356, "Gene Expression from Adeno-associated Virus Vectors in Airway Epithelial Cells".
Duff et al. (1995) Nature 373:476, "Mouse model made".
Flotte et al. (1993) J. Biol. Chem. 268:3781-3790, "Expression of the Cystic Fibrosis Transmembrane Conductance Regulator from a Novel Adeno-associated Virus Promoter".
Games et al. (1995) Nature 373:523, "Alzheimer-type neuropathology in transgenic mice overexpressing V717F beta-amyloid precursor protein".
Gething et al. (1981) Nature, 293:620-625, "Cell-surface expression of influenza haemagglutin from a cloned DNA copy of the RNA gene".
Green et al. (1994) Nature Genetics 7:13-21, "Antigen-Specific Human Monoclonal Antibodies From Mice Engineered With Human Ig Heavy and Light Chains YACs".
Goate et al. (1991) Nature 349:704, Segregation of a missense mutation in the amyloid precursor protein gene with familial Alzheimer's diease.
Gorfien et al. (2003) Biopharm. International 16(4):34 "Optimized Nutrient Additives for Fed-Batch Cultures".
Graham and van der Erb (1973) Virology 52:456-457, "A New Techique for the Assay of Infectivity of Human Adenovirus 5 DNA".
Graham et al. (1977) J. Gen Virol. 36:59, "Characteristics of a Human Cell Line Transformed by DNA from Human Adenovirus Type 5".
Haj-Ahmand and Graham (1986) J. Virol. 57:267, "Development of a Helper-Independent Human Adenovirus Vector and Its Use in the Transfer of the Herpes Simplex Virus Thymidine Kinase Gene".
Hardy (1997) TINS 20:154-159, "Amyloid, the Presenilins and Alzheimer's Disease".
Hawley-Nelson and Ciccarone (2003) Current Protocols in Cell Biology, J. Wiley & Sons, Unit 206, "Transfection of Eukaryotic Cells Using Cationic Lipid Reagents".

Hermonat et al. (1984) Proc. Natl. Acad. Sci. USA 81:6466-6470, "Use of adeno-associated virus as a mammalian DNA cloning vector: Transduction of neomycin resistance into mammalian tissue culture cells".
Herz and Gerard (1993) Proc. Natl. Acad. Sci. USA 90:2812-2816, "Adenovirus-mediated transfer of low density lipoprotein receptor gene acutely accelerates cholesterol clearance in normal mice".
Huston et al. (1988) Proc. Natl. Acad. Sci. U.S.A. 85:5879-83, "Protein engineering of antibody binding sites: Recovery of specific activity in an anti-digoxin single-chain Fv analogue produced in *Escherichia coli*".
Johnson-Wood et al. (1997) Proc. Natl. Acad. Sci. USA 94:1550-1555,"Amyloid precursor protein processing and Abeta42 deposition in a transgenic mouse model of Alzheimer disease".
Kaufman et al. (1987) EMBO J. 6:187-195, "Translational effiency of polycistronic mRNAs and their utilization to express heterologous genes in mammalian cells".
Keown et al. (1990) Methods in Enzymology 185:527-537, "Methods for Introducing DNA into Mammalian Cells".
Kostelny et al. (1992) J. Immunol. 148:1547-1553, "Formation of a Bispecific Antibody by the Use of Leucine Zippers".
Kozbor et al. (1983) Immunology Today, 4(3):72-79, "The Production of Monoclonal antibodies from Human Lymphocytes".
Lao and Toth (1997) Biotechnology. Prog. 13(5): 688-691, "Effect of ammonium and lactate on growth and metabolism of a recombinant Chinese Hamster Ovary Cell Culture".
Lemarchand et al. (1992) Proc. Natl. Acad. Sci. USA 89:6482-6486, "Adenovirus-mediated transfer of a recombinant human alphal-antitrypsin cDNA to human endothelial cells".
Mader, S. And White, J. H (1993) Proc. Natl. Acad. Sci. USA 90:5603-5607, "A steroid-inducible promoter for the controlled overexpression of cloned genes in eukaryotic cells".
Moloney et al. (2000) Journal of Biol. Chem. 275(13):964-9611, "Mammalian Notch1 Is Modified with Two Unusual Forms of O-Linked Glycosylation Found on Epidermal Growth Factor-like Modules".
Manome et al. (1993) Biochemistry 32(40):10607-10613, "Coinduction of c-jun gene expression and internucleosomal DNA fragmentation by ionizing radiation".
Mansour et al. (1988) Nature 336:348-352, "Disruption of the proto-oncogene int-2 in mouse embryo derived stem cells: a general strategy for targeting mutations to non-selectable genes".
Mantei et al. (1979) Nature 281:40-46, "Rabbit beta-globin mRNA production in mouse L cells transformed with cloned rabbit beta-globin chromosomal DNA".
Mather (1980) Biol. Reprod. 23:243-252, "Establishment and Characterization of Two Distinct Mouse Testicular Epithelial Cell Lines".
Mather et al. (1982) Annals N.Y. Acad. Sci. 383:44-68, "Culture of Testicular Cells in Hormone Supplemented Serum-Free Medium".
McLaughlin et al. (1989) J. Virol. 62:1963-1973, "Adeno-Associated Virus General Transduction Vectors: Analysis of Proviral Structures".
Miller, A.D. (1990) Blood 76:271-278, "Progress Toward Human Gene Therapy".
Milligan, G. and Rees, S (1999) TIPS 20:118-124, "Chimaeric G alpha Proteins: their potential use in drug discovery".
Milstein et al. (1983) Nature 305(6):537-540, "Hybrid hybridomas and their use in immunohistochemistry".
Morrison et al. (1984) Proc. Natl. Acad. Sci. U.S.A. 81:6851-6855, "Chimeric human antibody molecules: Mouse antigen-binding domains with human constant region domains".
Morrison (1985) Science 229:1202-1207, "Transfectomas Provide Novel Chimeric Antibodies".
Mullan et al. (1992) Nature Genet. 1:345-347, "A pathogenic mutation for probable Alzheimer's disease in the APP gene at the N-terminus of beta-amyloid".
Murrell et al. (1991) Science 254:97-99, "A Mutation in the Amyloid Precursor Protein Associated with Hereditary Alzheimer's Disease".
Mustonen and Alitalo (1995) J. Cell Biol. 129:895-898, "Endothelial Receptor Tyrosine Kinases Involved in Angiogenesis".
Muzyczka et al. (1992) Curr. Topics in Micro. And Immunol. 158:97-129, "Use of Adeno-Associated Virus as a General Transduction Vector for Mammalian Cells".

Naismith and Sprang (1996) J. Inflamm. 47(1-2):1-7, "Tumor Necrosis Factor Receptor Superfamily".
Okayama, et al. (1985) Mol. Cell Biol. 5:1136-1142, "Bacteriophage Lambda Vector for Transducing a cDNA Clone Library into Mammalian".
Oi et al. (1986) BioTechniques 4:214, "Chimeric Antibodies".
Olsson et al. (1982) Meth. Enzymol. 92: 3-16, "Human-Human Monoclonal Antibody-Producing Hybridomas: Technical Aspects".
Quantin et al. (1992) Proc. Natl. Acad. Sci. USA 89:2581-2584, "Adenovirus as an expression vector in muscle cell in vivo".
Ravetch and Kinet (1991) Annu. Rev. Immunol 9:457-492, "Fc Receptors".
Rosenfeld et al. (1991) Science 252:431-434, "Adenovirus-Mediated Transfer of a Recombinant Alpha1-Antitrypsin Gene to the Lung Epithelium in Vivo".
Rosenfeld et al. (1992) Cell 68:143-155, "In vivo Transfer of the Human Cystic Fibrosis Transmembrane Conductance Regulator Gene to the Airway Epithelium".
Roth et al. (2001) Annals of the New York Academy of Sciences, 928:305-15, "Caloric Restriction in Primates and Relevance to Humans".
Samulski et al. (1989) J. Virol. 63(9):3822-3828, "Helper-Free Stocks of Recombinant Adeno Associated Viruses: Normal Integration Does Not Require Viral Gene Expression".
Sato et al. (1995) Nature 376(6535):70-74, "Distinct Roles of the Receptor Tyrosine Kinases Tie-1 and Tie-2 in Blood Vessel Formation".
Schenk et al. (1999) Nature 400:173-177, "Immunization with amyloid-beta attenuates Alzheimer disease-like pathology in the Pdapp mouse".
Seed, B (1987) Nature 329:840-842, "An LFA-3 cDNA encodes a phospholipid-linked membrane protein homologous to its receptor CD2".
Selkoe (1993) TINS 16:403-409, "Physiological production of the beta-amyloid protein and the mechanism of Alzheimer's disease".
Selkoe (1994) J. Neuropathol. Exp. Neurol. 53(5):438-447, "Alzheimer's Disease: A Central Role for Amyloid".
Shibuya et al. (1990) Oncogene 5:519-524, "Nucleotide Sequence and Expression of a Novel Human Receptor-type Tyrosine Kinase Gene (flt) Closely Related to the Fms Family".
Smith (1985) Science 228:1315-1317, "Filamentous Fusion Phage: Novel Expression Vectors That Display Cloned Antigens on the Virion Surface".
Songsivilai & Lachmann (1990) Clin. Exp. Immunol. 79:315-321, "Bispecific antibody: a tool for diagnosis and treatment of disease".
Spencer, D. M. et al. (1993) Science 262:1019-1024, "Controlling Signal Transduction with Synthetic Ligands".
Staunton et al. (1990) Cell 61:243-254, "The Arrangement of the Immunoglobulin-like Domains of ICAM-1 and the Binding Sited for the LFA-1 and Rhinovirus".
Takeda et al. (1985) Nature 314:452, "Constriction of Chimaeric Processed Immunoglobulin Genes Containing Mouse Variable and Human Constant Region Sequences".
Teng et al. (1983) Proc. Natl. Acad. Sci. U.S.A., 80: 7308-7312, "Construction and Testing of Mouse Human Heteromyelomas for Human Monoclonal Antibody Production".
Terman et al. (1991) Oncogene 6:1677-83, "Identification of a New Endothelial Cell Growth Factor Receptor Tyrosine Kinase".
Thomas et al. (1987) Cell 51:503-512, "Site-Directed Mutagenesis by Gene Targeting in Mouse Embryo-Derived Stem Cells".
Tomlinso et al. (1992) J. Mol. Biol. 227:776-798, "The Repertoire of Human Germline VH Sequences Reveals About Fifty Groups of VH Segments with Different Hypervariable Loops".
Tomlinson et al. (1995) EMBO J. 14:4628-4638, "The Structural Reperoire of the Human VK Domain".
Tratschin et al. (1985) Mol. Cell. Biol. 5(11):3251-3260, "Adeno-Associated Virus Vector for High Frquency Integration, Expression, and Rescue of Genes in Mammalian Cells".
Tratschin et al. (1985) Mol. Cell. Biol. 4(10):2072-2081, "A Human Parvovirus, Adeno-Associated Virus, as a Eucaryotic Vector: Transient Expression and Encapsidation of the Procaryotic Gene for Chloramphenicol Acetyltransferase".
Tratschin et al. (1984) J. Virol. 51(3):611-619, "Genetic Analysis of Adeno-Associated Virus: Properties of Deletion Mutants Constructed in Vitro and Evidence for an Adeno-Associated Virus Replication Function".
Urlaub and Chasin (1980) Proc. Natl. Acad. Sci. USA, 77(7):4216-4220, "Isolation of Chinese Hamster Cell Mutants Deficient in Dihydrofolate Reductase Activity".
Watson, S. And S. Arkinstall (1994) The G-Protein Linked Receptor Facts Book, Academic Press, San Diego Calif., pp. 130-132.
Wilson et al. (1992) J. Biol. Chem. 267(2):963-967, "Hepatocyte-directed Gene Transfer in Vivo Leads to transient Improvement of Hyprecholesterolemia in Low Density Lipoprotein Receptor-defient Rabbits".
Wondisford et al. (1988) Mol. Endocrinol. 2:32-39, "Cloning of the Human Thyrotropin beta-Subunit Gene and Transient Expression of Biologically Active Human Thyrotropin after Gene Transfection".
Wu, G. And Wu, C. H. (1988) J. Biol. Chem. 263(29):14621-14624, "Receptor-mediated Gene Delivery and Expression in Vivo".
Yarden and Ullrich (1988) Ann. Rev. Biochem. 57:433-478, "Growth Factor Receptor Tyrosine Kinases".
Halicka et al (1995) Cancer Research, American Association for Cancer Research 55:444-449, "2-Deoxy-D-Glucose Enhances Sensitivity of Human Histiocytic Lymphoma U937 Cells to Apoptosis Induced by Tumor Necrosis Factor".

* cited by examiner

Figure 1. Figure 1 shows Cell Growth of α-GDF-8 Cells in the Presence of 2-Deoxyglucose in Dishes.
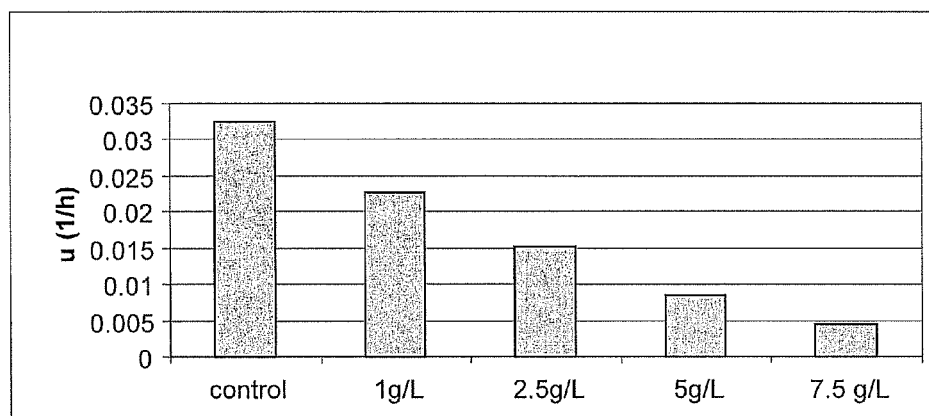
Figure 2. Cell Growth of α-GDF-8 Cells in 1L Bioreactors With and Without 2-Deoxyglucose.
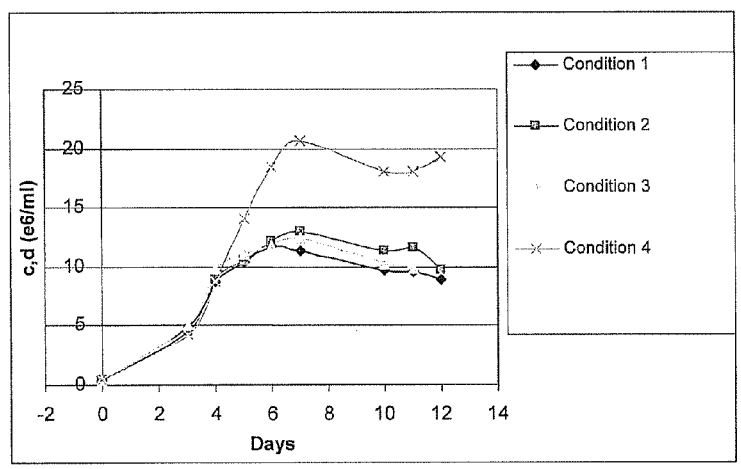

Figure 3. Viability of α-GDF-8 Cells in 1L Bioreactors With and Without 2-Deoxyglucose.
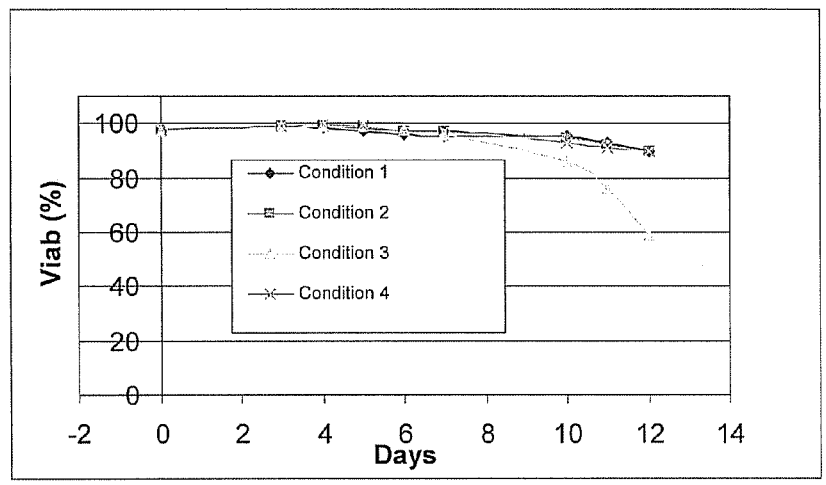
Figure 4. Lactate Accumulation of α-GDF-8 Cells in 1L Bioreactors With and Without 2-Deoxyglucose.
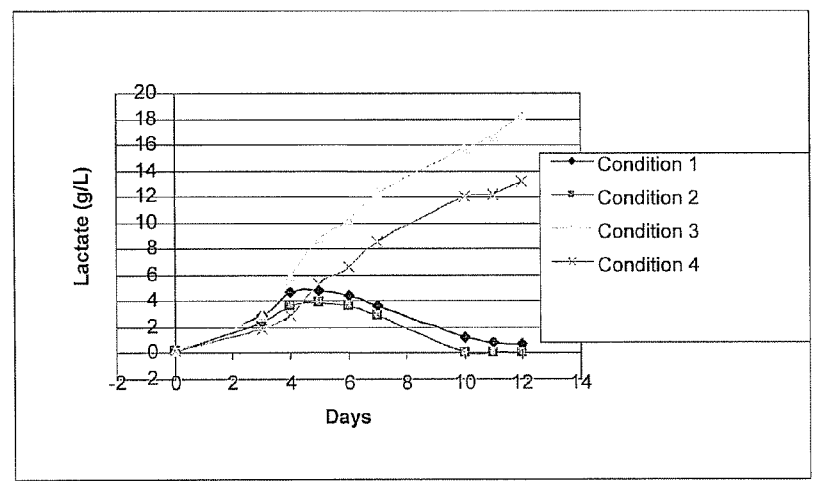

Figure 5. Titer of α-GDF-8 Cells in 1L Bioreactors With and Without 2-Deoxyglucose.
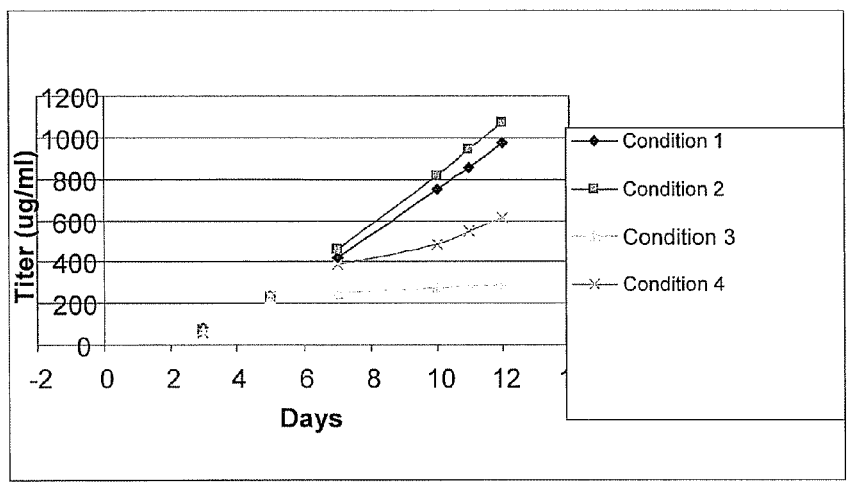
Figure 6. Cell Growth of α-GDF-8 Cells in 1L Bioreactors With and Without 2-Deoxyglucose.
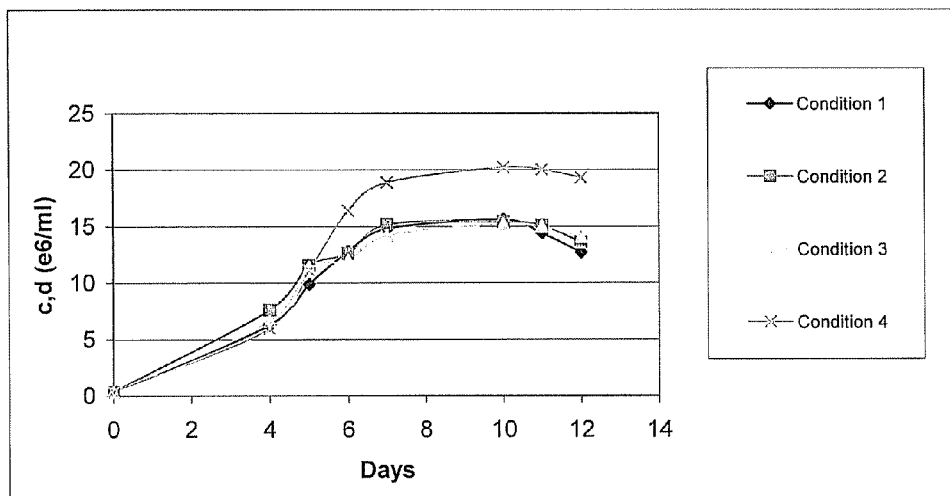

Figure 7. Lactate Accumulation of α-GDF-8 Cells in 1L Bioreactors With and Without 2-Deoxyglucose.
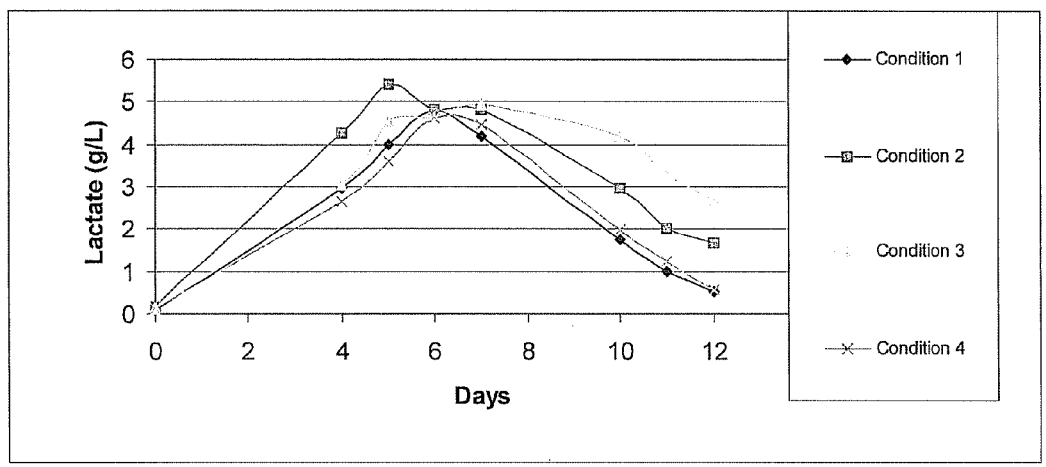
Figure 8. Titer of α-GDF-8 Cells in 1L Bioreactors With and Without 2-Deoxyglucose.
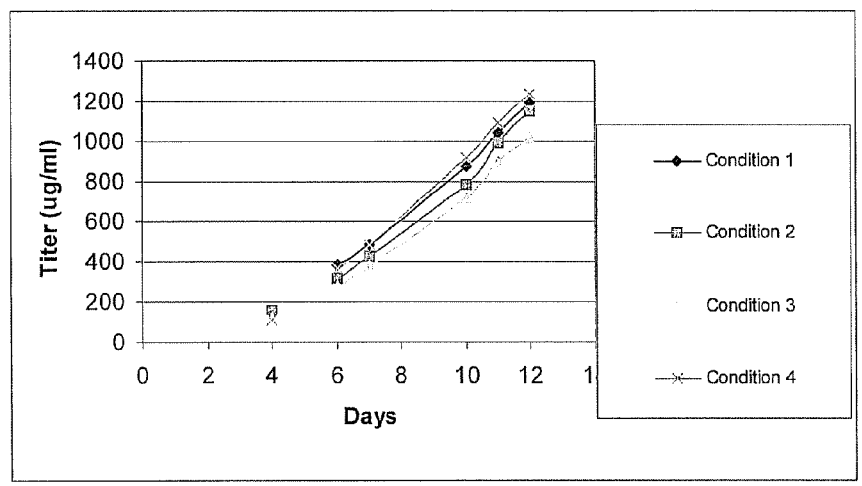

Figure 9. Glucose Uptake of α-GDF-8 Cells in 1L Bioreactors With and Without 2-Deoxyglucose.
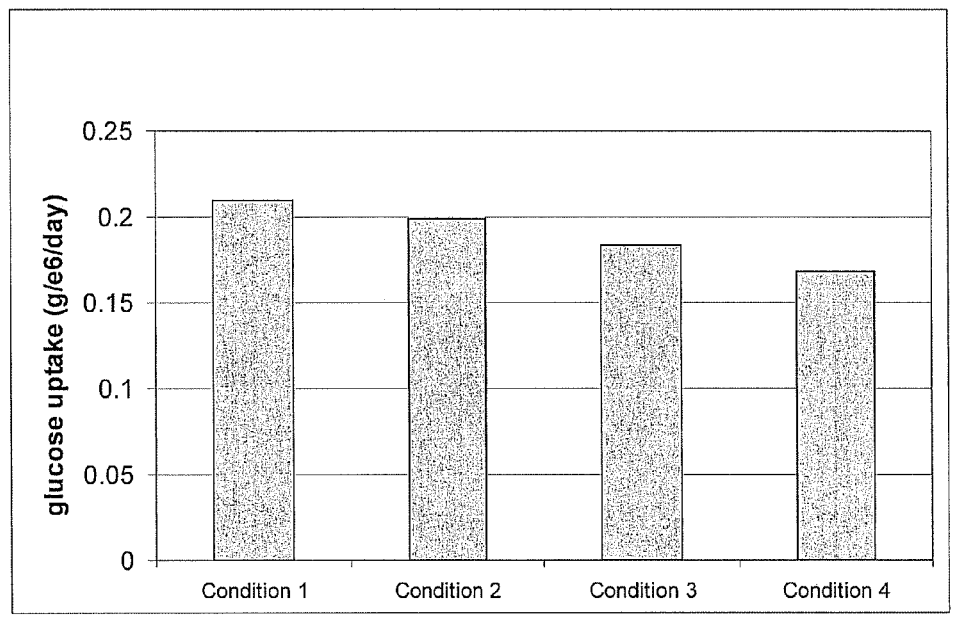
Figure 10. Daily Viable Cell Density of α-GDF-8 Cells in the Presence and Absence of 2-Deoxyglucose.
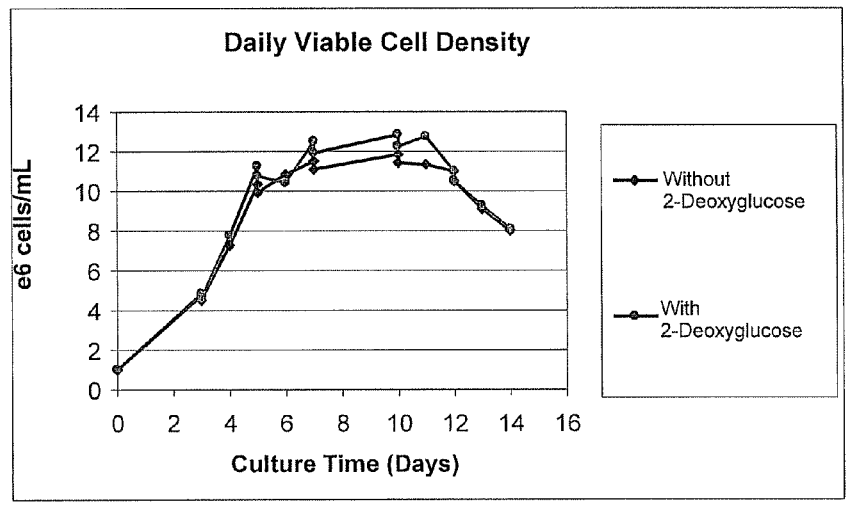

Figure 11. Daily Titer of α-GDF-8 Cells in the Presence and Absence of 2-Deoxyglucose.
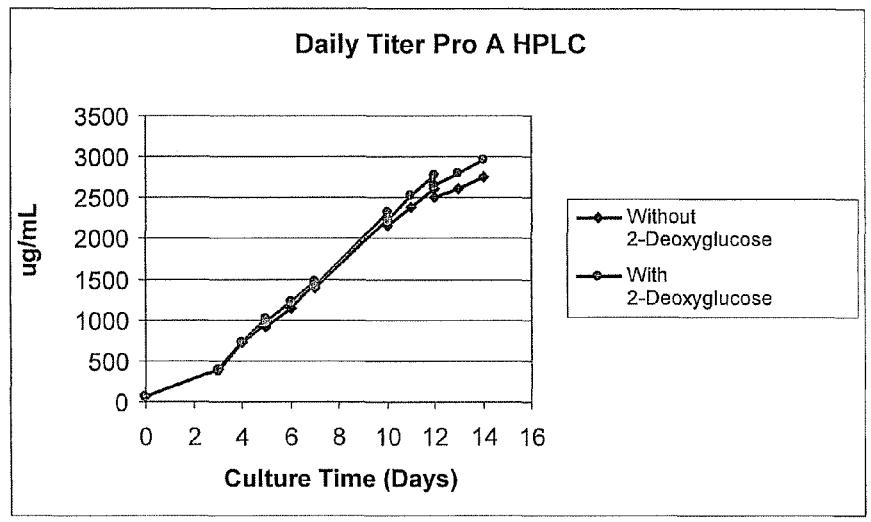
Figure 12. Daily Lactate Levels of α-GDF-8 Cells in the Presence and Absence of 2-Deoxyglucose.
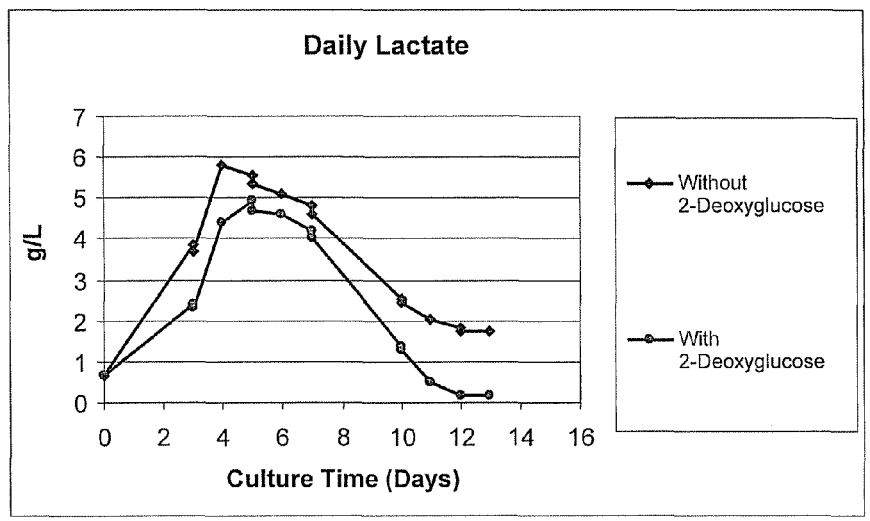

Figure 13. Daily Glucose Levels of α-GDF-8 Cells in the Presence and Absence of 2-Deoxyglucose.
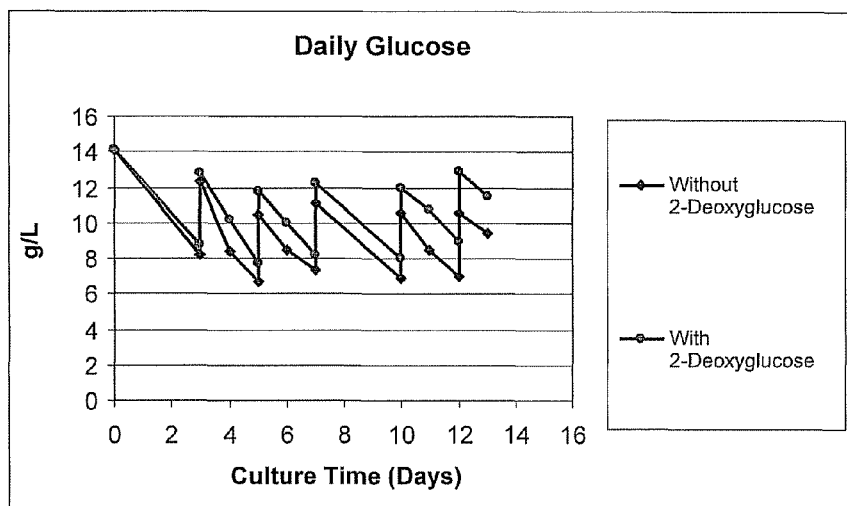
Figure 14. Daily Specific Productivity of α-GDF-8 Cells in the Presence and Absence of 2-Deoxyglucose.
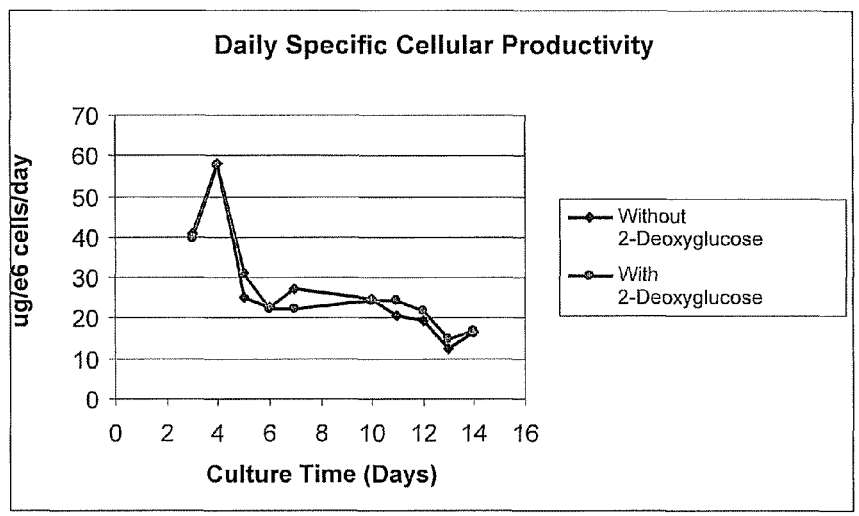

GLYCOLYSIS-INHIBITING SUBSTANCES IN CELL CULTURE

CROSS-REFERENCE TO RELATED APPLICATIONS

This application is copending with, shares at least one common inventor with, and claims priority to U.S. Provisional Patent Application No. 60/856,615 filed Nov. 3, 2006, the entire contents of which are hereby incorporated by reference.

BACKGROUND OF THE INVENTION

Proteins and polypeptides have become increasingly important therapeutic and commercial agents. In most cases, these proteins and polypeptides are produced in cell culture, from cells that have been engineered and/or selected to produce unusually high levels of the particular protein or polypeptide of interest. Control and optimization of cell culture conditions is critically important for successful commercial production of proteins and polypeptides.

Many proteins and polypeptides produced in cell culture are made in a batch or fed-batch process, in which cells are cultured for a period of time, and then the culture is terminated and the produced protein or polypeptide is isolated. Alternatively, proteins or polypeptides can be produced in a perfusion cell culture process in which the culture is not terminated and new nutrients and other components are periodically added to the culture, and during which the expressed protein or polypeptide is harvested periodically. The ultimate amount and quality of protein or polypeptide produced can be dramatically affected by the conditions of the cell culture. For example, traditional batch and fed-batch culture processes often result in production of metabolic waste products that have detrimental effects on cell growth or viability, and on production or stability of the protein or polypeptide of interest. Among these detrimental waste products is the glucose metabolite lactate. Lactate accumulation has been shown to reduce the pH of the cell culture, and is detrimental to both cell viability and productivity (see Gorfien et al., Optimized Nutrient Additives for Fed-Batch Cultures, *Biopharm. International*, April 2003). While a variety of efforts have been made to improve production of proteins and polypeptides in cell culture processes, there remains a need for additional improvements.

Furthermore, significant effort has been invested in the development of defined media (i.e., media assembled from known individual components and lacking serum or other animal byproducts) for use in culturing cells, particularly mammalian cells. Cell growth characteristics can be very different in defined media as contrasted with serum-derived media. There is a particular need for the development of improved systems for producing proteins and polypeptides by cell culture in defined media, in which the accumulation of detrimental waste products is reduced or eliminated.

SUMMARY OF THE INVENTION

The present invention provides improved methods and compositions for large scale production of proteins and/or polypeptides in cell culture. In certain embodiments, a cell culture medium containing a glycolysis-inhibiting substance is provided. In certain embodiments, a cell culture medium containing the glucose analog 2-deoxyglucose is provided. In certain embodiments, a cell culture medium containing di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and/or fluoroacetate is provided. In certain embodiments, a cell culture medium containing a glycolysis-inhibiting substance, in which glutamine is present at a concentration that is less than approximately 13 mM, is provided. In certain embodiments, a cell culture medium containing glycolysis-inhibiting substance, in which glutamine is present at a concentration that is less than approximately 4 mM, is provided. In certain embodiments, cell culture media of the present invention are used to grow mammalian cells that express a protein or polypeptide of interest.

In certain embodiments, the present invention provides commercial scale (e.g., 500 L or more) culture methods that utilize a medium containing a glycolysis-inhibiting substance, e.g. 2-deoxyglucose, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, and/or fluoroacetate. In certain embodiments, the culture methods as disclosed may include one or more temperature shifts during the course of the cell culture. According to the teachings herein, use of such methods allows high levels of protein production and lessens accumulation of certain undesirable factors including, but not limited to, lactate.

One of ordinary skill in the art will understand that the media formulations of the present invention encompass both defined and complex media. In certain embodiments, the culture medium is a defined medium in which the composition of the medium is known and controlled.

In certain embodiments, cells are grown in accordance with any of the cell culture methods described in U.S. patent application Ser. Nos. 11/213,308, 11/213,317 and 11/213,633 each of which was filed Aug. 25, 2005, and each of which is herein incorporated by reference in its entirety. In some embodiments, the cells are grown under one or more of the conditions described in U.S. Provisional Patent Application Ser. No. 60/830,658, filed Jul. 13, 2006 and incorporated herein by reference in its entirety.

Cell cultures of the present invention may optionally be supplemented with nutrients and/or other medium components including for example hormones and/or other growth factors, ions (such as sodium, chloride, calcium, magnesium, and/or phosphate), buffers, vitamins, nucleosides or nucleotides, trace elements (inorganic compounds usually present at very low final concentrations), amino acids, lipids, and/or glucose or other energy sources. In certain embodiments, it is beneficial to supplement the media with one or more chemical inductants such as hexamethylene-bis(acetamide) ("HMBA") and sodium butyrate ("NaB"). These optional supplements may be added at the beginning of the culture or may be added at a later point in order to replenish depleted nutrients or for another reason. In general, it is desirable to select the initial medium composition to minimize supplementation in accordance with the present invention.

BRIEF DESCRIPTION OF THE DRAWING

FIG. 1 shows Cell Growth of α-GDF-8 Cells in the Presence of 2-Deoxyglucose in Dishes.

FIG. 2 shows Cell Growth of α-GDF-8 Cells in 1 L Bioreactors With and Without 2-Deoxyglucose.

FIG. 3 shows Viability of α-GDF-8 Cells in 1 L Bioreactors With and Without 2-Deoxyglucose.

FIG. 4 shows Titer of α-GDF-8 Cells in 1 L Bioreactors With and Without 2-Deoxyglucose.

FIG. 5 shows Lactate Accumulation of α-GDF-8 Cells in 1 L Bioreactors With and Without 2-Deoxyglucose.

FIG. 6 shows Cell Growth of α-GDF-8 Cells in 1 L Bioreactors With and Without 2-Deoxyglucose.

FIG. 7 shows Titer of α-GDF-8 Cells in 1 L Bioreactors With and Without 2-Deoxyglucose.

FIG. 8 shows Lactate Accumulation of α-GDF-8 Cells in 1 L Bioreactors With and Without 2-Deoxyglucose.

FIG. 9 shows Glucose Uptake of α-GDF-8 Cells in 1 L Bioreactors With and Without 2-Deoxyglucose.

FIG. 10 shows Daily Viable Cell Density of α-GDF-8 Cells in the Presence and Absence of 2-Deoxyglucose.

FIG. 11 shows Daily Titer of α-GDF-8 Cells in the Presence and Absence of 2-Deoxyglucose.

FIG. 12 shows Daily Lactate Levels of α-GDF-8 Cells in the Presence and Absence of 2-Deoxyglucose.

FIG. 13 shows Daily Glucose Levels of α-GDF-8 Cells in the Presence and Absence of 2-Deoxyglucose.

FIG. 14 shows Daily Specific Productivity of α-GDF-8 Cells in the Presence and Absence of 2-Deoxyglucose.

DEFINITIONS

"Amino acid": The term "amino acid" as used herein refers to any of the twenty naturally occurring amino acids that are normally used in the formation of polypeptides, or analogs or derivatives of those amino acids or any non-naturally occurring amino acid. Amino acids of the present invention are provided in medium to cell cultures. Amino acids provided in the medium may be provided as salts or in hydrate form.

As used herein, the term "antibody" includes a protein comprising at least one, and typically two, VH domains or portions thereof, and/or at least one, and typically two, VL domains or portions thereof. In certain embodiments, the antibody is a tetramer of two heavy immunoglobulin chains and two light immunoglobulin chains, wherein the heavy and light immunoglobulin chains are inter-connected by, e.g., disulfide bonds. The antibodies, or a portion thereof, can be obtained from any origin, including, but not limited to, rodent, primate (e.g., human and non-human primate), camelid, as well as recombinantly produced, e.g., chimeric, humanized, and/or in vitro generated, as described in more detail herein.

Examples of binding fragments encompassed within the term "antigen-binding fragment" of an antibody include, but are not limited to, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized heavy chain variable domain (VHH); (vii) a single chain Fv (scFv); (viii) a bispecific antibody; and (ix) one or more fragments of an immunoglobulin molecule fused to an Fc region. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-26; Huston et al. (1988) Proc. Natl. Acad. Sci. U.S.A. 85:5879-83). Such single chain antibodies are also intended to be encompassed within the term "antigen-binding fragment" of an antibody. These fragments may be obtained using conventional techniques known to those skilled in the art, and the fragments are evaluated for function in the same manner as are intact antibodies.

The "antigen-binding fragment" can, optionally, further include a moiety that enhances one or more of, e.g., stability, effector cell function or complement fixation. For example, the antigen binding fragment can further include a pegylated moiety, albumin, or a heavy and/or a light chain constant region.

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

Numerous methods known to those skilled in the art are available for obtaining antibodies or antigen-binding fragments thereof. For example, monoclonal antibodies may be produced by generation of hybridomas in accordance with known methods. Hybridomas formed in this manner are typically screened using standard methods, such as enzyme-linked immunosorbent assay (ELISA) and surface plasmon resonance (Biacore™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In certain embodiments, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, published Oct. 31, 1996, and PCT Application No. PCT/US96/05928, filed Apr. 29, 1996.

In certain embodiments, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096 B. Humanized antibodies may also be produced, for example, using transgenic mice that express human heavy and light chain genes, but are incapable of expressing the endogenous mouse immunoglobulin heavy and light chain genes. Winter describes an exemplary CDRgrafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Such methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. A recombinant DNA encoding a humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982), and may be made according to the teachings of PCT Publication WO92/06193 or EP 0239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) J. Mol. Biol. 227:776-798; Cook, G. P. et al. (1995) Immunol. Today Vol. 16 (5): 237-242; Chothia, D. et al. (1992) J. Mol. Biol. 227:799-817; and Tomlinson et al. (1995) EMBO J. 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In certain embodiments, an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, Annu. Rev. Immunol 9:457-92, 1991; Capel et al., Immunomethods 4:25-34, 1994; and de Haas et al., J. Lab. Clin. Med. 126:330-41, 1995).

"Batch culture": The term "batch culture" as used herein refers to a method of culturing cells in which all the components that will ultimately be used in culturing the cells, including the medium (see definition of "Medium" below) as well as the cells themselves, are provided at the beginning of the culturing process. A batch culture is typically stopped at some point and the cells and/or components in the medium are harvested and optionally purified.

"Bioreactor": The term "bioreactor" as used herein refers to any vessel useful for the growth of a cell culture. A bioreactor can be of any size so long as it is useful for the culturing of cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. A bioreactor can be composed of any material that is suitable for holding cell cultures suspended in media under the culture conditions of the present invention, including glass, plastic or metal. The term "production bioreactor" as used herein refers to the final bioreactor used in the production of the polypeptide or protein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

"Cell density": The term "cell density" as used herein refers to that number of cells present in a given volume of medium.

"Cell viability": The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

"Complex medium": The term "complex medium" as used herein refers to a medium contains at least one component whose identity or quantity is either unknown or uncontrolled.

"Culture", "Cell culture": These terms as used herein refer to a cell population that is suspended in a medium (see definition of "Medium" below) under conditions suitable to survival and/or growth of the cell population. As will be clear to those of ordinary skill in the art, these terms as used herein also refer to the combination comprising the cell population and the medium in which the population is suspended. In certain embodiments, the cell culture is a mammalian cell culture.

"Defined medium": The term "defined medium" as used herein refers to a medium in which the composition of the medium is both known and controlled.

"Fed-batch culture": The term "fed-batch culture" as used herein refers to a method of culturing cells in which additional components are provided to the culture at a time or times subsequent to the beginning of the culture process. The provided components typically comprise nutritional supplements for the cells which have been depleted during the culturing process. Additionally or alternatively, the additional components may include supplementary components (see definition of "Supplementary components" below). In certain embodiments, the additional components may be provided in a feed medium (see definition of "Feed medium" below). A fed-batch culture is typically stopped at some point and the cells and/or components in the medium are harvested and optionally purified.

"Feed medium": The term "feed medium" as used herein refers to a solution containing nutrients which nourish growing mammalian cells that is added after the beginning of the cell culture. A feed medium may contain components identical to those provided in the initial cell culture medium. Alternatively, a feed medium may contain one or more additional components beyond those provided in the initial cell culture medium. Additionally or alternatively, a feed medium may lack one or more components that were provided in the initial cell culture medium. In certain embodiments, one or more components of a feed medium are provided at concentrations or levels identical or similar to the concentrations or levels at which those components were provided in the initial cell culture medium. In certain embodiments, one or more components of a feed medium are provided at concentrations or levels different than the concentrations or levels at which those components were provided in the initial cell culture medium. In certain embodiments, a feed medium contains supplementary components (see definition of "Supplementary components" below).

"Fragment": The term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least about 4-5, 10, 15, 20, 25, 30, 35, 40, 45, 50 or more amino acids of the full-length polypeptide.

"Gene": The term "gene" as used herein refers to any nucleotide sequence, DNA or RNA, at least some portion of which encodes a discrete final product, typically, but not limited to, a polypeptide. Optionally, the term refers not only to the coding sequence that encodes the polypeptide or other discrete final product, but may also encompass regions preceding and/or following the coding sequence that modulate the basal level of expression (see definition of "Genetic control element" below), as well as intervening sequences ("introns") between individual coding segments ("exons").

"Genetic control element": The term "genetic control element" as used herein refers to any sequence element that modulates the expression of a product of a gene to which it is operably linked. Genetic control elements may function by either increasing or decreasing the expression levels of a gene product and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

"Glycolysis": The term "glycolysis" as used herein refers to the metabolic oxidation of glucose by cells. During glycolysis, glucose is oxidized to either lactate or pyruvate. Under aerobic conditions, the dominant product is pyruvate. When oxygen is depleted, the dominant glycolytic product is lactate. Certain objects of the present invention are to prevent or slow the production or accumulation of lactate in cell culture by altering the normal process of glycolysis. In certain embodiments, production or accumulation of lactate is prevented or slowed by growing cells in a cell culture comprising a glycolysis-inhibiting substance, e.g. 2-deoxyglucose, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and/or fluoroacetate.

"Glycolysis-inhibiting substance": The term "glycolysis-inhibiting substance" as used herein refers to a substance (e.g., a compound, polypeptide, drug, metabolite, etc.) that inhibits or otherwise negatively alters the glycolysis of glucose and the subsequent production or accumulation of lactate. In certain embodiments, such a glycolysis-inhibiting substance is provided in a cell culture medium. In certain embodiments, a glycolysis-inhibiting substance is 2-deoxyglucose. In certain embodiments, a glycolysis-inhibiting substance is di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and/or fluoroacetate. One of ordinary skill in the art will recognize or will be able to determine glycolysis-inhibiting substances without undue experimentation that may be used in accordance with methods and compositions of the present invention.

"Host cell": The term "host cell" as used herein refers to a cell that is grown in culture according to the present invention to produce a protein or polypeptide of interest. In certain embodiments, the host cell is a mammalian cell.

"Hybridoma": The term "hybridoma" as used herein refers to a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature,* 537:3053, 1983).

"Integrated Viable Cell Density", "IVCD": The terms "integrated viable cell density" or "IVCD" as used herein refer to the average density of viable cells over the course of the culture multiplied by the amount of time the culture has run. When the amount of polypeptide and/or protein produced is proportional to the number of viable cells present over the course of the culture, integrated viable cell density is a useful tool for estimating the amount of polypeptide and/or protein produced over the course of the culture.

"Medium", "Cell culture medium", "Culture medium": These terms as used herein refer to a solution containing nutrients that nourish growing cells. In certain embodiments, the culture medium is useful for growing mammalian cells. Typically, a culture medium provides essential and non-essential amino acids, vitamins, energy sources, lipids, and trace elements required by the cell for minimal growth and/or survival. A culture medium may also contain supplementary components (see definition of "Supplementary components" below) that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, a medium is advantageously formulated to a pH and salt concentration optimal for cell survival and proliferation. In certain embodiments, the medium is a feed medium that is added after the beginning of the cell culture (see definition of "Feed medium", above). In certain embodiments, the cell culture medium is a mixture of a starting nutrient solution and any feed medium that is added after the beginning of the cell culture.

"Metabolic waste product": The term "metabolic waste product" as used herein refers to a compound produced by the cell culture as a result of normal or non-normal metabolic processes that are in same way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, glycosylation or other post-translational modification of the expressed polypeptide or protein, or may be detrimental to the cells and/or expression or activity of the recombinant polypeptide or protein in any number of other ways. Exemplary metabolic waste products include lactate, which is produced as a result of glucose metabolism, and ammonium, which is produced as a result of glutamine metabolism. A cell culture may produce one or more than one metabolic waste products. One goal of the present invention is to slow production of, reduce or even eliminate metabolic waste products in cell cultures.

"Polypeptide": The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. For example, a polypeptide may be glycosylated. A polypeptide to be expressed according to the present invention can be a polypeptide therapeutic. A polypeptide therapeutic is a polypeptide that has a biological effect on a region in the body on which it acts or on a region of the body on which it remotely acts via intermediates. Examples of polypeptide therapeutics are discussed in more detail below.

"Protein": The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit. A protein to be expressed according to the present invention can be a protein therapeutic. A protein therapeutic is a protein that has a biological effect on a region in the body on which it acts or on a region of the body on which it remotely acts via intermediates. Examples of protein therapeutics are discussed in more detail below.

"Recombinantly expressed polypeptide" and "Recombinant polypeptide": These terms as used herein refer to a polypeptide expressed from a host cell that has been manipulated by the hand of man to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

"Supplementary components": The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, supplementary components are added to the initial cell culture. In certain embodiments, supplementary components are added after the beginning of the cell culture.

"Titer": The term "titer" as used herein refers to the total amount of recombinantly expressed polypeptide or protein produced by a cell culture in a given amount of medium volume. Titer is typically expressed in units of milligrams or micrograms of polypeptide or protein per milliliter of medium.

DETAILED DESCRIPTION OF CERTAIN EMBODIMENTS

The present invention provides improved methods and media formulations for the production of proteins and/or polypeptides by cell culture. In certain embodiments, the invention provides methods that minimize production of metabolic waste products in a cell culture. In certain embodiments, the invention provides methods that minimize production of the metabolic waste product lactate. Lactate has been shown to be detrimental to cell growth, viability, and/or protein production or quality. Previous work has demonstrated that lactate levels in cell culture may be kept low by maintaining low glucose levels throughout the duration of the culture (Cruz et al., Metabolic Shifts by Nutrient Manipulation in Continuous Culture of BHK Cells, *Biotechnology and Bioengineering*, 66(2):104-13, 1999). However, continuous monitoring and adjustment of glucose levels is not practical for large-scale production of proteins or polypeptides. The present invention provides improved methods and media formulations for the production of proteins and/or polypeptides by cell culture that obviate the need to continuously monitor and adjust glucose levels of the culture. In certain embodiments, the cell culture is a batch or fed-batch culture.

Certain compositions of the present invention include a cell culture medium comprising a glycolysis-inhibiting substance. In certain embodiments, such glycolysis-inhibiting substances comprise 2-deoxyglucose, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, and/or fluoroacetate. According to some embodiments, levels of metabolic waste products of the culture are lower than levels of metabolic waste products produced under otherwise identical conditions in an otherwise identical medium that lacks such a glycolysis-inhibiting substance. According to some embodiments, lactate levels of the culture are lower than lactate levels produced under otherwise identical conditions in an otherwise identical medium that lacks such a glycolysis-inhibiting substance.

Other embodiments of the invention are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Cells

Any host cell susceptible to cell culture, and to expression of protein or polypeptides, may be utilized in accordance with the present invention. In certain embodiments, the host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2).

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of a protein or polypeptide of interest. Often, cells are manipulated to produce high levels of protein, for example by introduction of a gene encoding the protein or polypeptide of interest and/or by introduction of control elements that regulate expression of the gene (whether endogenous or introduced) encoding the polypeptide or protein of interest.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population may exist such that certain individual cells will grow better and/or produce more polypeptide of interest. In certain embodiments, the cell line is empirically selected by the practitioner for robust growth under the particular conditions chosen for culturing the cells. In certain embodiments, individual cells engineered to express a particular polypeptide are chosen for large-scale production based on cell growth, final cell density, percent cell viability, titer of the expressed polypeptide or any combination of these or any other conditions deemed important by the practitioner.

Culturing the Cells

The present invention may be used with any cell culture method or system that is amenable to the expression of polypeptides. For example, the cells may be grown in batch or fed-batch cultures, where the culture is terminated after sufficient expression of the polypeptide, after which the expressed polypeptide is harvested and optionally purified. Alternatively, the cells may be grown in perfusion cultures, where the culture is not terminated and new nutrients and other components are periodically or continuously added to the culture, during which the expressed polypeptide is periodically or continuously harvested.

The cells may be grown in any convenient volume chosen by the practitioner. For example, the cells may be grown in small scale reaction vessels ranging in volume from a few milliliters to several liters. Alternatively, the cells may be grown in large scale commercial Bioreactors ranging in volume from approximately least 1 liter to 10, 100, 250, 500, 1,000, 2,500, 5,000, 8,000, 10,000, 12,000 liters or more, or any volume in between The temperature of the cell culture will be selected based primarily on the range of temperatures at which the cell culture remains viable, at which a high level of polypeptide is produced, the temperature at which production or accumulation of metabolic waste products is minimized, and/or any combination of these or other factors deemed important by the practitioner. As one non-limiting example, CHO cells grow well and produce high levels or protein or polypeptide at approximately 37° C. In general, most mammalian cells grow well and/or can produce high levels or protein or polypeptide within a range of about 25° C. to 42° C., although methods taught by the present disclosure are not limited to these temperatures. Certain mammalian cells grow well and/or can produce high levels or protein or polypeptide within the range of about 35° C. to 40° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times during the cell culture process. Those of ordinary skill in the art will be able to select appropriate temperature or temperatures in which to grow cells, depending on the needs of the cells and the production requirements of the practitioner.

Furthermore, the culture may be subjected to one or more temperature shifts during the course of the culture. When shifting the temperature of the culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in these embodiments. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

As with the initial temperature or temperature range, the temperature or temperature range of the cell culture after the temperature shift(s) will be selected based primarily on the temperature(s) at which the cell culture remains viable, the range in which a high level of polypeptide or protein is produced, the range in which production or accumulation of metabolic waste products is minimized, and/or any combination of these or other factors deemed important by the practitioner. In general, most mammalian cells remain viable and produce high levels or protein or polypeptide within a range of about 25° C. to 42° C., although methods taught by the present disclosure are not limited to these temperatures. In certain embodiments, mammalian cells remain viable and produce high levels or protein or polypeptide within a range of about 25° C. to 35° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times after the temperature shift(s). Those of ordinary skill in the art will be able to select appropriate temperature(s) or temperature range(s) in which to grow cells after the temperature shift(s), depending on the particular needs of the cells and the particular production requirements of the practitioner. The cells may be grown for any amount of time, depending on the needs of the practitioner and the requirement of the cells themselves.

In certain embodiments, batch and fed-batch reactions are terminated once the expressed polypeptide reaches a sufficiently high titer, as determined by the needs of the practitioner. As non-limiting examples, cell cultures may be terminated when the polypeptide titer is 100, 200, 300, 400, 500, 600, 700, 800, 900, 1000, 1100, 1200, 1300, 1400, 1500, 2000 mg/L or higher. One of ordinary skill in the art will be able to select one or more appropriate titers at which a batch and/or fed-batch culture may be harvested. Additionally or alternatively, batch and fed-batch reactions are terminated once the cells reach a sufficiently high density, as determined by the needs of the practitioner. For example, the culture may be terminated once the cells reach 1, 5, 10, 15, 20, 25, 30, 35, 40, 45, 50, 55, 60, 65, 70, 75, 80, 85, 90, 95 or 99 percent of maximal viable cell density.

In certain embodiments, batch and/or fed-batch cell cultures are terminated to prevent the undesirable production or accumulation of metabolic waste products such as lactate and ammonium. In certain embodiments, a cell culture is terminated before lactate accumulates in the culture to an undesirable level. As non-limiting examples, a cell culture may be terminated before lactate reaches 8, 7, 6, 5, 4, 3, 2, or 1 g/L. In certain embodiments, cell cultures grown in accordance with methods and compositions of the present invention are able to grow for a longer period of time than would be possible using traditional culture methods since production or accumulation of metabolic waste products is minimized.

In certain embodiments, batch and fed-batch reactions are terminated once the cell density reaches a sufficiently high level, as determined by the needs of the practitioner. For example, a cell culture may be terminated once the cell density reaches 1, 2, 3, 4, 5, 6, 7, 8, 9, 10, 11, or 12 million cells per mL, or more. In certain embodiments, batch and fed-batch reactions are terminated before the cell density reaches 1 million cells per mL. In certain embodiments, cell cultures grown in accordance with methods and compositions of the present invention are able to grow to a higher cell density than would be possible using traditional culture methods.

In certain cases, it may be beneficial or necessary to supplement the cell culture during the subsequent production phase with nutrients or other medium components that have been depleted or metabolized by the cells. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. These supplementary components may all be added to the cell culture at one time, or they may be provided to the cell culture in a series of additions.

In certain embodiments, cells are grown in accordance with any of the cell culture methods described in U.S. patent application Ser. Nos. 11/213,308, 11/213,317 and 11/213, 633 each of which was filed Aug. 25, 2005, and each of which is herein incorporated by reference in its entirety. For example, in certain embodiments, the cells may be grown in a culture medium in which the cumulative amino acid concentration is greater than about 70 mM. In certain embodiments, the cells may be grown in a culture medium in which the molar cumulative glutamine to cumulative asparagine ratio is less than about 2. In certain embodiments, the cells may be grown in a culture medium in which the molar cumulative glutamine to cumulative total amino acid ratio is less than about 0.2. In certain embodiments, the cells may be grown in a culture medium in which the molar cumulative inorganic ion to cumulative total amino acid ratio is between about 0.4 to 1. In certain embodiments, the cells may be grown in a culture medium in which the combined cumulative glutamine and cumulative asparagine concentration is between about 16 and 36 mM. In certain embodiments, the cells may be grown in a culture medium that contains two, three, four or all five of the preceding medium conditions.

In some embodiments, the cells are grown under one or more of the conditions described in U.S. Provisional Patent Application Ser. No. 60/830,658, filed Jul. 13, 2006 and incorporated herein by reference in its entirety. For example, in some embodiments, cells are grown in a culture medium that contains manganese at a concentration between approximately 10 and 600 nM. In some embodiments, cells are grown in a culture medium that contains manganese at a concentration between approximately 20 and 100 nM. In some embodiments, cells are grown in a culture medium that contains manganese at a concentration of approximately 40 nM.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, final titer of the expressed polypeptide or any combination of these or other conditions deemed important by the practitioner.

Media Compositions

Any of a wide variety of growth media may be used in accordance with the present invention. In certain embodiments, the cells are grown in any of a variety of chemically defined media, wherein the components of the media are both known and controlled. In certain embodiments, the cells are grown in any of a variety of complex media, in which not all components of the medium are known and/or controlled.

Chemically defined growth media for cell culture have been extensively developed and published over the last several decades, including chemically defined growth media for mammalian cell culture. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive cell cultures that produce recombinant proteins and/or polypeptides.

Defined media typically consist of roughly fifty chemical entities at known concentrations in water. Most defined media also contain one or more well-characterized proteins such as insulin, IGF-1, transferrin or BSA, but others require no protein components and so are referred to as protein-free defined media. The chemical components of defined media generally fall into five broad categories: amino acids, vitamins, inorganic salts, trace elements, and a miscellaneous category that defies neat categorization.

All media, defined or complex, include an energy source for the growing cells. Often, the energy source is glucose, a simple monosaccharide sugar that has the chemical formula $C_6H_{12}O_6$. Traditional media formulations, including commercially available media such as Ham's F10 (Sigma), Minimal Essential Medium ([MEM], Sigma), RPMI-1640 (Sigma), and Dulbecco's Modified Eagle's Medium ([DMEM], Sigma), have contained relatively high levels of glucose. Glucose has traditionally been thought to be required in abundance since it is the primary metabolic energy sources for the cells. However, rapid consumption of glucose leads to the accumulation of lactate. Lactate is a detrimental metabolic waste product and is a known inhibitor of cell growth and productivity in cell culture (see Gorfien et al., Optimized Nutrient Additives for Fed-Batch Cultures, *Biopharm. International, April* 2003; Lao and Toth, Effect of ammonium and lactate on growth and metabolism of a recombinant Chinese Hamster Ovary Cell Culture, *Biotechnology. Prog.* 13(5): 688-691, 1997).

The present invention encompasses the discovery that certain cell culture methods and medium formulations minimize and even reverse accumulation of metabolic waste products, e.g. lactate, in the culture. Roth et al. have demonstrated that 2-deoxyglucose reduces glucose/energy flux when fed to rats without decreasing their total food intake (Caloric Restriction in Primates and Relevance to Humans, *Annals of the New York Academy of Sciences*, 928:305-15, 2001). 2-deoxyglucose is a structural analog of glucose in which the hydroxyl group at the 2' position of the sugar is replaced with a hydrogen moiety. This disclosure demonstrates that media formulations that contain glycolysis-inhibiting substances, including but not limited to 2-deoxyglucose, result in a decrease in the accumulation of metabolic waste products, including lactate, when used to grow cells in cell culture. Without wishing to be bound by any particular theory, it is possible that by providing such a glycolysis-inhibiting substance in the starting media, glycolysis is slowed or altered in some way, thus slowing or preventing the accumulation of lactate in the culture. Media formulations of the present invention that contain such glycolysis-inhibiting substances also have beneficial effects on cell growth and/or viability, leading to a higher overall IVCD.

In certain embodiments, a glycolysis-inhibiting substance to be used in accordance with the present invention comprises 2-deoxyglucose. In certain embodiments, 2-deoxyglucose is provided at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40, 45, 50 or more grams per liter. In certain embodiments, the ratio of 2-deoxyglucose to glucose in the cell culture is 1/50, 1/45, 1/40, 1/39, 1/38, 1/37, 1/36, 1/35, 1/34, 1/33, 1/32, 1/31, 1/30, 1/29, 1/28, 1/27, 1/26, 1/25, 1/24, 1/23, 1/22, 1/21, 1/20, 1/19, 1/18, 1/17, 1/16, 1/15, 1/14, 1/13, 1/12, 1/11, 1/10, 1/9, 1/8, 1/7, 1/6, 1/5, 1/4, 1/3, 1/2, 1/1 or any ratio higher or lower than these. One of ordinary skill in the art will understand that the foregoing concentrations and ratios of 2-deoxyglucose in a cell culture medium may be achieved using a batch culture, a fed-batch culture, or a perfusion culture.

The present invention also encompasses medium formulations in which the concentration of glutamine is limited. In certain embodiments, the concentration of glutamine in the cell culture medium is limited to less than approximately 13 mM. In certain embodiments, the concentration of glutamine in the cell culture medium is limited to less than approximately 4 mM.

Metabolic waste products (e.g. lactate) accumulate over time as cells are grown in culture. As described above, cell cultures grown according to teachings described herein may optionally be temperature shifted to a lower temperature after an initial growth phase at a higher temperature. An interesting and beneficial result of utilizing a starting medium in which the concentration of glutamine is limited is that lactate levels stop increasing and actually begin to decrease upon shifting the cell culture to a lower temperature (for example, see Examples 3 and 4). Without wishing to be bound by any particular theory, it is possible that cells grown under low glutamine conditions as taught by the present invention may actually begin consuming and/or processing lactate.

According to the teachings described herein, it is generally desirable to grow a cell culture in which the total IVCD is high. By providing a culture medium in which the concentration of glutamine is limited and shifting the cell culture to a lower temperature after an initial growth phase, the levels of lactate in the culture begin to decrease, potentially permitting a more viable and/or dense cell culture. One problem with this strategy is that if the temperature is shifted too late, the cells will be unable to take up lactate, resulting in a less viable and/or less dense cell culture. Thus, it is desirable to shift the culture to a lower temperature before lactate accumulates to a critical level. However, a negative effect of shifting the cells to the lower temperature too early is that cell growth is consequently slowed. Thus, traditional cell culture methods force practitioners to choose between two less than ideal options: 1) shifting the culture early, resulting in a lower overall accumulation (and subsequent decrease if grown under low glutamine conditions) of lactate but a decreased cell growth rate after the early temperature shift, or 2) shifting the culture later, resulting an increased cell growth rate but a higher overall accumulation of lactate.

The present disclosure demonstrates that one benefit of growing cells in a cell culture medium that contains a glycolysis-inhibiting substance, e.g. 2-deoxyglucose, is that lactate accumulates at a slower rate than it would in a comparable culture medium that lacks such a glycolysis-inhibiting substance. As a result, the culture may be shifted to a lower temperature at a later point than would be possible if the culture lacked such a glycolysis-inhibiting substance, with the result that the cells will still begin to take up lactate after the shift. Thus, by utilizing certain inventive media and methods described herein, cell density will be higher at the time of the shift and the total IVCD will be increased.

The present disclosure teaches that at least two factors may be important in determining when to shift the culture to ensure that the cells begin to take up lactate after the shift: the lactate concentration at the time of the shift and the cell density at the time of the shift (e.g., see Example 3). Particular cell lines may produce different amounts of lactate, or may be more or less resistant to lactate that has accumulated in the culture. Regardless, utilization of the inventive methods and media compositions described herein will result in a lower overall accumulation of lactate in any given cell culture, thus allowing the culture to be shifted to a lower temperature at a later time point and increasing the total IVCD of the culture. One of ordinary skill in the art will be able to select the exact time point at which the culture is shifted to the lower temperature based on the character of the cell line used, the character of the protein or polypeptide to be produced, the presence or absence of other components in the medium or any other factor that is desirable to his or her experimental and/or other needs.

Inventive media formulations disclosed herein may optionally be supplemented as necessary or desirable with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, protein hydrolysates, or glucose or other energy source. In certain embodiments of the present invention, it may be beneficial to supplement the media with chemical inductants such as hexamethylene-bis(acetamide) ("HMBA") and/or sodium butyrate ("NaB"). These optional supplements may be added at the beginning of the culture or may be added at a later point in order to replenish depleted nutrients or for another reason. One of ordinary skill in the art will be aware of any desirable or necessary supplements that may be included in media formulations of the present invention and will be able to select which particular supplements to add based on his or her experimental and/or other needs.

Polypeptides

Any polypeptide that is expressible in a host cell may be produced in accordance with the methods and compositions disclosed herein. The polypeptide may be expressed from a gene that is endogenous to the host cell, or from a heterologous gene that is introduced into the host cell. The polypeptide may be one that occurs in nature, or may alternatively have a sequence that was engineered or selected by the hand of man. A polypeptide to be produced may be assembled from polypeptide fragments that individually occur in nature. Additionally or alternatively, the engineered polypeptide may include one or more fragments that are not naturally occurring.

Polypeptides that may desirably be expressed in accordance with the present invention will often be selected on the basis of an interesting or useful biological or chemical activity. In certain embodiments, methods and/or compositions of the present invention are employed to express a protein therapeutic or polypeptide therapeutic. For example, the present invention may be employed to express any pharmaceutically or commercially relevant enzyme, receptor, antibody, hormone, regulatory factor, antigen, binding agent etc. The following list of polypeptides and proteins that can be produced according to the present invention is merely exemplary in nature, and is not intended to be a limiting recitation. One of ordinary skill in the art will understand that any polypeptide or protein may be expressed in accordance with the present invention and will be able to select the particular polypeptide to be produced based on his or her particular needs.

Clotting Factors

Clotting factors have been shown to be effective as pharmaceutical and/or commercial agents. Given the importance of recombinant clotting factors in the treatment of diseases such as Hemophilia, optimizing the expression of recombinantly produced clotting factors in accordance with methods and compositions of the present invention is of particular interest. One non-limiting example of a clotting factor that can be produced in accordance with the present invention is Coagulation Factor IX (Factor IX, or "FIX"). FIX is a single-chain glycoprotein whose deficiency results in Hemophilia B, a disorder in which the blood of the sufferer is unable to clot. Thus, any small wound that results in bleeding is potentially a life-threatening event.

FIX is synthesized as a single chain zymogen that can be activated to a two-chain serine protease (Factor IXa) by release of an activation peptide. The catalytic domain of Factor IXa is located in the heavy chain (see Chang et al., J. Clin. Invest., 100:4, 1997, incorporated herein by reference). FIX has multiple glycosylation sites including both N-linked and O-linked carbohydrates. One particular O-linked structure at Serine 61 (Sia-$\alpha$2,3-Gal-$\beta$1,4-GlcNAc-$\beta$1,3-Fuc-$\alpha$1-O-Ser) was once thought unique to FIX but has since found on a few other molecules including the Notch protein in mammals and Drosophila (Maloney et al, Journal of Biol. Chem., 275(13), 2000). FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain zymogen and then processed into a two-chain active form. The present invention may also be employed to control or alter the glycosylation pattern of clotting factor VIII in order to modulate its clotting activity. Other glycoprotein clotting factors that can be produced and whose glycosylation pattern can be controlled or altered in accordance with the present invention include for example, but are not limited to, tissue factor and von Willebrands factor.

Antibodies

Antibodies are proteins that have the ability to specifically bind a particular antigen. Given the large number of antibodies currently in use or under investigation as pharmaceutical or other commercial agents, production of antibodies in accordance with methods and compositions of the present invention is of particular interest.

Any antibody that can be expressed in a host cell may be used in accordance with the present invention. In certain embodiments, an antibody to be expressed is a monoclonal antibody. In certain embodiments, the monoclonal antibody is a chimeric antibody. As is known in the art, a chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, each of which is incorporated herein by reference in its entirety.

In certain embodiments, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the hypervariable region are replaced with residues from a non-human species that confer a desired antigen specificity or affinity. In certain embodiments, a humanized antibody has an amino acid sequence that is at least 80, 85, 90, 91, 92, 93, 94, 95, 96, 97, 98, 99 percent identical or higher to a human antibody. In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olsson et al., *Meth. Enzymol.*, 92: 3-16, 1982), and may be made according to the teachings of PCT Publication WO92/06193 or EP 0239400, each of which is incorporated herein by reference in its entirety).

As but one non-limiting example, an antibody that may be produced according to the present teachings is an anti-ABeta antibody. Anti-ABeta antibodies are a particularly promising potential avenue of therapy in the treatment of Alzheimer's disease ("AD"). AD is a progressive disease resulting in senile dementia (see generally: Selkoe, TINS 16:403, 1993; Hardy et al., WO 92/13069; Selkoe, J. Neuropathol. Exp. Neurol. 53:438, 1994; Duff et al., Nature 373:476, 1995; Games et al., Nature 373:523, 1995, each of which is incorporated herein by reference). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 µm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed ABeta or Beta-amyloid peptide. ABeta peptide is a 4-kDa internal fragment of 39-43 amino acids of a larger transmembrane glycoprotein named protein termed amyloid precursor protein (APP). As a result of proteolytic processing of APP by different secretase enzymes, ABeta is primarily found in both a short form, 40 amino acids in length, and a long form, ranging from 42-43 amino acids in length. Part of the hydrophobic transmembrane domain of APP is found at the carboxy end of ABeta, and may account for the ability of ABeta to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of AD (see, e.g., Goate et al., Nature 349:704, 1991 (valine717 to isoleucine); Chartier Harlan et al. Nature 353:844, 1991 (valine717 to glycine); Murrell et al., Science 254:97, 1991 (valine717 to phenylalanine); Mullan et al., Nature Genet. 1:345, 1992 (a double mutation changing lysine595-methionine596 to asparagine595-leucine596), each of which is incorporated herein by reference in its entirety). Such mutations are thought to cause AD by increased or altered processing of APP to ABeta, particularly processing of APP to increased amounts of the long form of ABeta (i.e., ABeta1-42 and ABeta1 43). Mutations in other genes, such as the presenilin genes, PS1 and PS2, are thought indirectly to affect processing of APP to generate increased amounts of long form ABeta (see Hardy, TINS 20: 154, 1997, incorporated herein by reference in its entirety).

Mouse models have been used successfully to determine the significance of amyloid plaques in AD (Games et al., supra; Johnson-Wood et al., Proc. Natl. Acad. Sci. USA 94:1550, 1997, incorporated herein by reference in its entirety). In particular, when PDAPP transgenic mice, (which express a mutant form of human APP and develop Alzheimer's disease at a young age), are injected with the long form of ABeta, they display both a decrease in the progression of Alzheimer's and an increase in antibody titers to the ABeta peptide (Schenk et al., Nature 400, 173, 1999, incorporated herein by reference in its entirety). The observations discussed above indicate that ABeta, particularly in its long form, is a causative element in Alzheimer's disease.

The ABeta peptide can exist in solution and can be detected in CNS (e.g., CSF) and plasma. Under certain conditions, soluble ABeta is transformed into fibrillary, toxic, Beta-sheet forms found in neuritic plaques and cerebral blood vessels of patients with AD. Treatments involving immunization with monoclonal antibodies against ABeta have been investigated. Both active and passive immunization have been tested as in mouse models of AD. Active immunization resulted in some reduction in plaque load in the brain, but only by nasal administration. Passive immunization of PDAPP transgenic mice has also been investigated (Bard, et al., Nat. Med. 6:916-19, 2000, incorporated herein by reference in its entirety). It was found that antibodies recognizing the amino-terminal and central domains of ABeta stimulated phagocytosis of ABeta deposits, whereas antibodies against domains near the carboxy-terminal domain did not.

The mechanism of clearance of ABeta after passive or active immunization is under continued investigation. Two mechanisms have been proposed for effective clearance, i.e., central degradation and peripheral degradation. The central degradation mechanism relies on antibodies being able to cross the blood-brain barrier, bind to plaques, and induce clearance of pre-existing plaques. Clearance has been shown to be promoted through an Fc-receptor-mediated phagocytosis (Bard, et al., supra). The peripheral degradation mechanism of ABeta clearance relies on a disruption of the dynamic equilibrium of ABeta between brain, CSF, and plasma upon administration of antibody, leading to transport of ABeta from one compartment to another. Centrally derived ABeta is transported into the CSF and the plasma where it is degraded. Recent studies have concluded that soluble and unbound ABeta are involved in the memory impairment associated with AD, even without reduction in amyloid deposition in the brain. Further studies are needed to determine the action and/or interplay of these pathways for ABeta clearance (Dodel, et al., The Lancet Vol. 2:215, 2003, incorporated herein by reference in its entirety).

Anti-ABeta antibodies are a potentially promising route of treatment of AD since they may bind to and clear the ABeta or other components that comprise the amyloid plaques. Anti-ABeta antibodies produced in accordance with the teachings of the present disclosure may serve to better treat AD or other related diseases by, for example, binding and clearing components of amyloid plaques more effectively, by clearing amyloid plaques with fewer or less severe side effects, or by preventing formation or build-up of amyloid plaques. In certain embodiments, anti-ABeta antibodies produced in accordance with the present teachings are monoclonal antibodies.

In certain embodiments, anti-ABeta antibodies produced in accordance with the present teachings bind specifically to the aggregated form of ABeta without binding to the soluble form. In certain embodiments, anti-ABeta antibodies produced in accordance with the present teachings bind specifically to the soluble form of anti-ABeta under conditions at which they do not bind to the aggregated form. In certain embodiments, anti-ABeta antibodies produced in accordance with the present teachings bind to both aggregated and soluble forms. In certain embodiments, anti-ABeta antibodies produced in accordance with the present teachings bind ABeta in plaques. In certain embodiments, anti-ABeta antibodies produced in accordance with the present teachings cross the blood-brain barrier. In certain embodiments, anti-ABeta antibodies produced in accordance with the present teachings reduce amyloid burden in a subject. In certain embodiments, anti-ABeta antibodies produced in accordance with the present teachings reduce neuritic dystrophy in a subject. In certain embodiments, anti-ABeta antibodies can maintain synaptic architecture (e.g., synaptophysin).

According to some embodiments, anti-ABeta antibodies produced in accordance with the present teachings bind to an epitope within residues 13-28 of ABeta (with the first N terminal residue of natural ABeta designated 1). In some embodiments, anti-ABeta antibodies produced in accordance with the present teachings bind to an epitope within residues 19-22 of ABeta. In some embodiments, multiple monoclonal antibodies having binding specificities to different anti-ABeta epitopes are used. For example, in some embodiments, an antibody specific for an epitope within residues 19-22 of ABeta is co-administered with an antibody specific for an epitope outside of residues 19-22 of ABeta. Such antibodies can be administered sequentially or simultaneously. Antibodies to amyloid components other than ABeta can also be used (e.g., administered or co-administered).

In certain embodiments, anti-ABeta antibodies produced in accordance with the present teachings bind to an ABeta epitope more strongly or with more specificity than anti-ABeta antibodies otherwise produced. Epitope specificity of an antibody can be determined by known techniques, for example, by forming a phage display library in which different members display different subsequences of ABeta. The phage display library may then be selected for members specifically binding to an antibody under test. A family of sequences is isolated. Typically, such a family contains a common core sequence, and varying lengths of flanking sequences in different members. The shortest core sequence showing specific binding to the antibody typically defines the epitope bound by the antibody. Alternatively or additionally, antibodies may be tested for epitope specificity in a competition assay with an antibody whose epitope specificity has already been determined. For example, antibodies that compete with the 15C11 antibody for binding to ABeta are considered to bind to the same or similar epitope as 15C11, i.e., within residues ABeta 19-22. In certain embodiments, screening antibodies for epitope specificity is a useful predictor of therapeutic efficacy. For example, an antibody determined to bind to an epitope within residues 13-28 (e.g., to Aβ 19-22) of ABeta is likely to be effective in preventing and treating Alzheimer's disease according to the methodologies of the present invention.

Antibodies that specifically bind to a preferred segment of ABeta without binding to other regions of ABeta have a number of advantages relative to monoclonal antibodies binding to other regions, or to polyclonal sera to intact ABeta. Among other things, for equal mass dosages, dosages of antibodies that specifically bind to preferred segments contain a higher molar dosage of antibodies effective in clearing amyloid plaques. Also, antibodies specifically binding to preferred segments may induce a clearing response against amyloid deposits without inducing a clearing response against intact APP polypeptide, thereby reducing the potential side effects.

In certain embodiments, the monoclonal, chimeric, single-chain or humanized antibodies described above may contain amino acid residues that do not naturally occur in any antibody in any species in nature. These foreign residues can be utilized, for example, to confer novel or modified specificity, affinity or effector function on the monoclonal, chimeric, single-chain or humanized antibody.

Enzymes

Another class of polypeptides that have been shown to be effective as pharmaceutical and/or commercial agents and that can desirably be produced according to the teachings of the present invention includes enzymes. Given the importance of recombinant enzymes in the treatment of diseases and other commercial and pharmaceutical uses, production of enzymes in accordance with the present invention is of particular interest.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892, incorporated herein by reference in its entirety). Thus, production of GCR in accordance with methods of the present invention is contemplated. Those of ordinary skill in the art will be aware of other desirable enzymes that may be produced in accordance with methods of the present invention.

Growth Factors and Other Signaling Molecules

Another class of polypeptides that have been shown to be effective as pharmaceutical and/or commercial agents and that can desirably be produced according to the teachings of the present invention includes growth factors and other signaling molecules. Given the biological importance of growth factors and other signaling molecules and their importance as potential therapeutic agents, production of these molecules in accordance with methods and compositions of the present invention is of particular interest. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; bone morphogenetic proteins (BMP); interferons such as interferon-alpha, -beta, and -gamma; colony stimulating factors (CSFs), e.g., M-CSF, GM-CSF, and G-CSF; interleukins (TLs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; plasminogen activators, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with the present invention.

Receptors

Another class of polypeptides that have been shown to be effective as pharmaceutical and/or commercial agents and that can desirably be produced according to the teachings of the present invention includes receptors. Given the biological importance of receptors and their importance as potential therapeutic agents, production of these molecules in accordance with methods and compositions of the present invention is of particular interest. Receptors are typically transmembrane glycoproteins that function by recognizing an extra-cellular signaling ligand. Receptors often have a protein kinase domain in addition to the ligand recognizing domain. This protein kinase domain initiates a signaling pathway by phosphorylating target intracellular molecules upon binding the ligand, leading to developmental or metabolic changes within the cell.

In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, *J Inflamm.* 47(1-2): 1-7, 1995-96, incorporated herein by reference in its entirety).

According to some embodiments, a tumor necrosis factor inhibitor comprises a soluble TNF receptor. In certain embodiments, a tumor necrosis factor inhibitor comprises a soluble TNFR-Ig. In certain embodiments, TNF inhibitors of the present invention are soluble forms of TNFRI and TNFRII. In certain embodiments, TNF inhibitors of the present invention are soluble TNF binding proteins. In certain embodiments, TNF inhibitors of the present invention are TNFR-Ig fusion proteins, e.g., TNFR-Fc or etanercept. As used herein, "etanercept," refers to TNFR-Fc, which is a dimer of two molecules of the extracellular portion of the p75 TNF-α receptor, each molecule consisting of a 235 amino acid Fc portion of human IgG1.

In certain embodiments, receptors to be produced in accordance with the present invention are receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, incorporated herein by reference). Non-limiting examples of RTKs include tumor necrosis factor alpha and beta receptors (TNFR-1; EP 417,563 published Mar. 20, 1991; and TNFR-2, EP 417,014 published Mar. 20, 1991; for review, see Naismith and Sprang, *J Inflamm.* 47(1-2):1-7, 1995-96, incorporated herein by reference), members of the fibroblast growth factor (FGF) receptor family, members of the epidermal growth factor receptor (EGF) family, platelet derived growth factor (PDGF) receptor, tyrosine kinase with immunoglobulin and EGF homology domains-I (TIE-1) and TIE-2 receptors (Sato et al., *Nature* 376(6535):70-74, 1995, incorporated herein be reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2 (VEGFR-2)), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Ax1. Those of ordinary skill in the art will be aware of other receptors that can be expressed in accordance with certain methods and compositions of the present invention.

In certain embodiments, the receptor to be produced in accordance with the present invention is a G-protein coupled receptor (GPCR). GPCRs are a major target for drug action and development. In fact, receptors have led to more than half of the currently known drugs (Drews, *Nature Biotechnology,* 14:1516, 1996) and GPCRs represent the most important target for therapeutic intervention with 30% of clinically prescribed drugs either antagonizing or agonizing a GPCR (Milligan, G. and Rees, S., *TIPS,* 20:118-124, 1999). Since these receptors have an established, proven history as therapeutic targets, production of GPCRs in accordance with the present invention is also of particular interest.

GPCRs are proteins that have seven transmembrane domains. Upon binding of a ligand to a GPCR, a signal is transduced within the cell which results in a change in a biological or physiological property of the cell. GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of *D. discoideum*; and Family V, the fungal mating pheromone receptors such as STE2.

GPCRs include receptors for biogenic amines, for lipid mediators of inflammation, peptide hormones, and sensory signal mediators. The GPCR becomes activated when the receptor binds its extracellular ligand. Conformational changes in the GPCR, which result from the ligand-receptor interaction, affect the binding affinity of a G protein to the GPCR intracellular domains. This enables GTP to bind with enhanced affinity to the G protein.

Activation of the G protein by GTP leads to the interaction of the G protein α subunit with adenylate cyclase or other second messenger molecule generators. This interaction regulates the activity of adenylate cyclase and hence production of a second messenger molecule, cAMP. cAMP regulates phosphorylation and activation of other intracellular proteins. Alternatively, cellular levels of other second messenger molecules, such as cGMP or eicosinoids, may be upregulated or downregulated by the activity of GPCRs. The G protein a subunit is deactivated by hydrolysis of the GTP by GTPase, and the α, β and γ subunits reassociate. The heterotrimeric G protein then dissociates from the adenylate cyclase or other second messenger molecule generator. Activity of GPCR may also be regulated by phosphorylation of the intra- and extracellular domains or loops.

Glutamate receptors form a group of GPCRs that are important in neurotransmission. Glutamate is the major neurotransmitter in the CNS and is believed to have important roles in neuronal plasticity, cognition, memory, learning and some neurological disorders such as epilepsy, stroke, and neurodegeneration (Watson, S, and S. Arkinstall, The G-Protein Linked Receptor Facts Book, Academic Press, San Diego Calif., pp. 130-132, 1994). The vasoactive intestinal polypeptide (VIP) family is a group of related polypeptides whose actions are also mediated by GPCRs. Key members of this family are VIP itself, secretin, and growth hormone releasing factor (GRF). VIP has a wide profile of physiological actions including relaxation of smooth muscles, stimulation or inhibition of secretion in various tissues, modulation of various immune cell activities, and various excitatory and inhibitory activities in the CNS. Secretin stimulates secretion of enzymes and ions in the pancreas and intestine and is also present in small amounts in the brain.

In general, practitioners of the present invention will selected their polypeptide of interest, and will know its precise amino acid sequence. Any given protein that is to be expressed in accordance with the present invention will have its own particular characteristics and may influence the cell density or viability of the cultured cells, and may be expressed at lower levels than another polypeptide or protein grown under identical culture conditions. One of ordinary skill in the art will be able to appropriately modify inventive media and methods described herein in order to optimize cell growth and/or production of any given expressed polypeptide or protein.

Introduction of Genes for the Expression of Polypeptide into Host Cells

In certain embodiments, a nucleic acid molecule introduced into the cell encodes the polypeptide desired to be expressed according to the present invention. In certain embodiments, a nucleic acid molecule may encode a gene product that induces the expression of the desired polypeptide by the cell. For example, the introduced genetic material may encode a transcription factor that activates transcription of an endogenous or heterologous polypeptide. Alternatively or additionally, the introduced nucleic acid molecule may increase the translation or stability of a polypeptide expressed by the cell.

Methods suitable for introducing nucleic acids sufficient to achieve expression of a polypeptide of interest into mammalian host cells are known in the art. See, for example, Gething et al., *Nature,* 293:620-625, 1981; Mantei et al., *Nature,* 281: 40-46, 1979; Levinson et al. EP 117,060; and EP 117,058, each of which is incorporated herein by reference. For mammalian cells, common methods of introducing genetic material into the cell include the calcium phosphate precipitation method of Graham and van der Erb, Virology, 52:456-457, 1978 or the Lipofectamine™ (Gibco BRL) Method of Hawley-Nelson, Focus 15:73, 1993. General aspects of mammalian cell host system transformations have been described by Axel in U.S. Pat. No. 4,399,216 issued Aug. 16, 1983. For various techniques for introducing genetic material into mammalian cells, see Keown et al., *Methods in Enzymology,* 185:527-537, 1990, and Mansour et al., *Nature,* 336:348-352, 1988.

In certain embodiments, the nucleic acid to be introduced is in the form of a naked nucleic acid molecule. In some aspects of these embodiments, the nucleic acid molecule introduced into a cell consists only of the nucleic acid encoding the polypeptide and the necessary genetic control elements. In some aspects of these embodiments, the nucleic acid encoding the polypeptide (including the necessary regulatory elements) is contained within a plasmid vector. Non-limiting representative examples of suitable vectors for expression of polypeptide in mammalian cells include pcDNA1; pCD, see Okayama, et al., *Mol. Cell Biol.* 5:1136-1142, 1985; pMClneo Poly-A, see Thomas, et al., *Cell* 51:503-512, 1987; a baculovirus vector such as pAC 373 or pAC 610; CDM8 (Seed, B., *Nature* 329:840, 1987) and pMT2PC (Kaufman, et al., EMBO J. 6:187-195, 1987). In certain embodiments, the nucleic acid molecule to be introduced into a cell is contained within a viral vector. For example, the nucleic acid encoding the polypeptide may be inserted into the viral genome (or a partial viral genome). The regulatory elements directing the expression of the polypeptide can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Additionally or alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (i.e., by electroporation). In some embodiments, naked DNA is introduced into cells by mixing the DNA with a liposome suspension containing cationic lipids. The DNA/liposome complex is then incubated with cells. Naked DNA can also be directly injected into cells by, for example, microinjection.

Additionally or alternatively, naked DNA can be introduced into cells by complexing the DNA to a cation, such as polylysine, which is coupled to a ligand for a cell-surface receptor (see for example Wu, G. and Wu, C. H., *J. Biol. Chem.* 263:14621, 1988; Wilson et al., *J. Biol. Chem.* 267: 963-967, 1992; and U.S. Pat. No. 5,166,320). Binding of the DNA-ligand complex to the receptor facilitates uptake of the DNA by receptor-mediated endocytosis.

Use of viral vectors containing particular nucleic acid sequences, e.g., a cDNA encoding a polypeptide, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D., *Blood* 76:271, 1990). A recombinant retrovirus can be constructed having a nucleic acid encoding a polypeptide of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a polypeptide of interest but is inactivated in terms of its ability to replicate in a normal lytic viral life cycle. See, for example, Berkner et al., *BioTechniques* 6:616, 1988; Rosenfeld et al., *Science* 252:431-434, 1991; and Rosenfeld et al., *Cell* 68:143-155, 1992. Suitable adenoviral vectors derived from the adenovirus strain Ad type 5 dl324 or other strains of adenovirus (e.g., Ad2, Ad3, Ad7 etc.) are known in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., *Proc. Natl. Acad. Sci. USA* 89:6482-6486, 1992), hepatocytes (Herz and Gerard, *Proc. Natl. Acad. Sci. USA* 90:2812-2816, 1993) and muscle cells (Quantin et al., *Proc. Natl. Acad. Sci. USA* 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra; Haj-Ahmand and Graham, *J. Virol* 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al., *Curr. Topics in Micro. and Immunol.* 158:97-129, 1992). It is also one of the few viruses that may integrate its DNA into non-dividing cells, and exhibits a high frequency of stable integration (see for example Flotte et al., *Am. J. Respir. Cell. Mol. Biol.* 7:349-356, 1992; Samulski et al., *J. Virol.* 63:3822-3828, 1989; and McLaughlin et al., *J. Virol.* 62:1963-1973, 1989). Vectors containing as little as 300 base pairs of AAV can be packaged and can integrate. Space for exogenous DNA is limited to about 4.5 kb. An AAV vector such as that described in Tratschin et al., (*Mol. Cell. Biol.* 5:3251-3260, 1985) can be used to introduce DNA into cells. A variety of nucleic acids have been introduced into different cell types using AAV vectors (see for example Hermonat et al., *Proc. Natl. Acad. Sci. USA* 81:6466-6470, 1984; Tratschin et al., *Mol. Cell. Biol.* 4:2072-2081, 1985; Wondisford et al., *Mol. Endocrinol.* 2:32-39, 1988; Tratschin et al, *J. Virol.* 51:611-619, 1984; and Flotte et al., *J. Biol. Chem.* 268:3781-3790, 1993).

When the method used to introduce nucleic acid molecules into a population of cells results in modification of a large proportion of the cells and efficient expression of the polypeptide by the cells, the modified population of cells may be used without further isolation or subcloning of individual cells within the population. That is, there may be sufficient production of the polypeptide by the population of cells such that no further cell isolation is needed and the population can be immediately be used to seed a cell culture for the production of the polypeptide. In some embodiments, it may be desirable to isolate and expand a homogenous population of cells from a single cell that efficiently produces the polypeptide.

Alternative to introducing a nucleic acid molecule into a cell that encodes a polypeptide of interest, an introduced nucleic acid may encode another polypeptide, protein or regulatory element that induces or increases the level of expression of the protein or polypeptide produced endogenously by a cell. For example, a cell may be capable of expressing a particular polypeptide but may fail to do so without additional treatment of the cell. Similarly, the cell may express insufficient amounts of the polypeptide for the desired purpose. Thus, an agent that stimulates expression of the polypeptide of interest can be used to induce or increase expression of that polypeptide by the cell. For example, an introduced nucleic acid molecule may encode a transcription factor that activates or upregulates transcription of the polypeptide of interest. Expression of such a transcription factor in turn leads to expression, or more robust expression, of the polypeptide of interest. Similarly, the introduced nucleic acid molecule may contain one or more regulatory elements that titrate away one or more transcriptional repressors from a regulatory region of the polypeptide of interest.

In certain embodiments, a nucleic acid that directs expression of the polypeptide is stably introduced into the host cell. In certain embodiments, a nucleic acid that directs expression of the polypeptide is transiently introduced into the host cell. One of ordinary skill in the art will be able to choose whether to stably or transiently introduce the nucleic acid into the cell based on his or her experimental needs.

A gene encoding the polypeptide of interest may optionally be linked to one or more regulatory genetic control elements. In some embodiments, a genetic control element directs constitutive expression of the polypeptide. In some embodiments, a genetic control element that provides inducible expression of a gene encoding the polypeptide of interest can be used. Use of an inducible genetic control element (e.g., an inducible promoter) allows for modulation of the production of the polypeptide in the cell. Non-limiting examples of potentially useful inducible genetic control elements for use in eukaryotic cells include hormone-regulated elements (see e.g., Mader, S, and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (see e.g., Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with methods and compositions described herein.

One of ordinary skill in the art will be able to choose and, optionally, to appropriately modify the method of introducing genes that cause the cell to express the polypeptide of interest in accordance with the teachings of the present invention.

Isolation of Expressed Polypeptide

In certain embodiments, it is desirable to isolate and/or purify proteins or polypeptides expressed according to the present invention. In certain embodiments, an expressed polypeptide or protein is secreted into the medium and thus cells and other solids may be removed, as by centrifugation or filtering for example, as a first step in the purification process.

In some embodiments, an expressed polypeptide or protein is bound to the surface of the host cell. In such embodiments, the media is removed and the host cells expressing the polypeptide or protein are lysed as a first step in the purification process. Lysis of mammalian host cells can be achieved by any number of means known to those of ordinary skill in the art, including physical disruption by glass beads and exposure to high pH conditions.

The polypeptide or protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, *Protein Purification Principles and Practice 2nd Edition*, Springer-Verlag, New York, 1987; Higgins, S. J. and Hames, B. D. (eds.), *Protein Expression: A Practical Approach*, Oxford Univ Press, 1999; and Deutscher, M. P., Simon, M. I., Abelson, J. N. (eds.), *Guide to Protein Purification: Methods in Enzymology*, Methods in Enzymology Series, Vol 182, Academic Press, 1997, each of which is incorporated herein by reference in its entirety). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. One of ordinary skill in the art will be aware of other know affinity tags useful for isolating the expressed polypeptide. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Use of protease inhibitors are often advantageous when cells must be lysed in order to isolate and purify the expressed polypeptide or protein.

One of ordinary skill in the art will appreciate that the exact purification technique may vary depending on the character of the polypeptide or protein to be purified, the character of the cells from which the polypeptide or protein is expressed, and the composition of the medium in which the cells were grown.

Immunogenic Compositions

Proteins or polypeptides produced according to the teachings of the present disclosure may also be used in immunogenic compositions, e.g., as vaccines. In general, selection of the appropriate "effective amount" or dosage for components of an inventive immunogenic composition(s) is typically based upon a variety of factors, including but not limited to, the identity of the selected polypeptide(s) in the immunogenic composition employed, the glycosylation pattern of the polypeptide(s), and the physical condition of the subject, most especially including the general health, age and weight of the immunized subject. As is known in the art, the particular methods and routes of administration and the presence of additional components in the immunogenic compositions may also affect the dosages and amounts of the DNA plasmid compositions. Such selection and upward or downward adjustment of the effective dose is within the skill of the art. The amount of immunogenic composition required to induce an immune response, including but not limited to a protective response, or produce an exogenous effect in the patient without significant adverse side effects varies depending upon these factors. Suitable doses are readily determined by persons skilled in the art.

Certain immunogenic compositions of the present invention may contain an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127, incorporated herein by reference in its entirety), 13, 14, 15, 16, 17 and 18 (and its mutant forms), the interferons-α, β and γ, granulocyte-macrophage colony stimulating factor (see, e.g., U.S. Pat. No. 5,078,996, incorporated herein by reference in its entirety), macrophage colony stimulating factor, granulocyte colony stimulating factor, GSF, and the tumor necrosis factors α and β. Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, K1LLER, TRAIL-R2, TRICK2, and DR6. Still another adjuvant molecule includes Caspase (ICE). See, also International Patent Publication Nos. WO98/17799 and WO99/43839, each of which is incorporated herein by reference in its entirety.

Also useful as adjuvants are cholera toxins (CT) and mutants thereof, including those described in published International Patent Application number WO 00/18434 (wherein the glutamic acid at amino acid position 29 is replaced by another amino acid (other than aspartic acid, for example a histidine). Similar CTs or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36). Each of these references is incorporated herein in its entirety.

In certain embodiments, immunogenic compositions of the present invention are administered to a human or to a non-human vertebrate by a variety of routes including, but not limited to, intranasal, oral, vaginal, rectal, parenteral, intradermal, transdermal (see for example, International patent publication No. WO 98/20734, which is hereby incorporated by reference in its entirety), intramuscular, intraperitoneal, subcutaneous, intravenous and intraarterial. The appropriate route may be selected depending on the nature of the immunogenic composition used, an evaluation of the age, weight, sex and general health of the patient and the antigens present in the immunogenic composition, and/or other factors known to those of ordinary skill in the art.

In certain embodiments, immunogenic compositions are administered at multiple times. The order of immunogenic composition administration and the time periods between individual administrations may be selected by one of skill in the art based upon relevant factors known to those of ordinary skill in the art, including but not limited to the physical characteristics and precise responses of the host to the application of the method.

Pharmaceutical Formulations

In certain embodiments, produced polypeptides or proteins will have pharmacologic activity and will be useful in the preparation of pharmaceuticals. Inventive compositions as described above may be administered to a subject or may first be formulated for delivery by any available route including, but not limited to parenteral, intravenous, intramuscular, intradermal, subcutaneous, oral, buccal, sublingual, nasal, bronchial, ophthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into compositions of the present invention. For example, a protein or polypeptide produced according to the present invention may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, US20040082764 A1). Additional ingredients useful in preparing pharmaceutical compositions in accordance with the present invention include, for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Alternatively or additionally, a protein or polypeptide produced according to the present invention may be administered in combination with (whether simultaneously or sequentially) one or more additional pharmaceutically active agents. An exemplary list of these pharmaceutically active agents can be found in the Physicians' Desk Reference, 55 Edition, published by Medical Economics Co., Inc., Montvale, N.J., 2001, incorporated herein by reference in its entirety. For many of these listed agents, pharmaceutically effective dosages and regimens are known in the art; many are presented in the Physicians' Desk Reference itself.

Solid pharmaceutical compositions may contain one or more solid carriers, and optionally one or more other additives such as flavoring agents, lubricants, solubilizers, suspending agents, fillers, glidants, compression aids, binders or tablet-disintegrating agents or an encapsulating material. suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier may be a finely divided solid which is in admixture with the finely divided active ingredient. In tablets, the active ingredient is generally mixed with a carrier having the necessary compression properties in suitable proportions, and optionally, other additives, and compacted into the desired shape and size.

Liquid pharmaceutical compositions may contain the polypeptide or protein expressed according to the present invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of, or limit the amount of, alcohol.

Examples of liquid carriers suitable for oral or parenteral administration include water (optionally containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

In certain embodiments, a pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Advantageously, certain pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain cases, it will be useful to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, advantageous methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier, e.g., for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such preparations may be mixed chewable or liquid formulations or food materials or liquids if desirable, for example to facilitate administration to children, to individuals whose ability to swallow tablets is compromised, or to animals. Formulations for oral delivery may advantageously incorporate agents to improve stability within the gastrointestinal tract and/or to enhance absorption.

For administration by inhalation, inventive compositions comprising a purified polypeptide or protein expressed from a mammalian cell line and a delivery agent can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered, for example a therapeutically effective amount. The present invention particularly contemplates delivery of inventive compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and inventive delivery agents will enhance cellular uptake. According to certain embodiments, compositions comprising a purified polypeptide expressed from a mammalian cell line and a delivery agent are formulated as large porous particles for aerosol administration.

Modified release and pulsatile release oral dosage forms may contain excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release oral dosage forms may contain one or a combination of release rate modifying excipients. Release rate modifying excipients may be present both within the dosage form i.e., within the matrix, and/or on the dosage form, i.e., upon the surface or coating.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Alternatively, the compounds can be administered in the form of a suppository or pessary, or they may be applied topically in the form of a gel, hydrogel, lotion or other glycerides, solution, cream, ointment or dusting powder.

In some embodiments, compositions are prepared with carriers that will protect the polypeptide or protein against rapid elimination from the body, such as a controlled release formulation, including implants and microencapsulated delivery systems. In general, inventive compositions may be formulated for immediate, delayed, modified, sustained, pulsed, or controlled-release delivery. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Suitable materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Proteins and polypeptides produced according to the present invention may also be used in combination with a cyclodextrin. Cyclodextrins are known to form inclusion and non-inclusion complexes with certain molecules. Formation of a cyclodextrin complex may modify the solubility, dissolution rate, bioavailability and/or stability property of a protein or polypeptide. Cyclodextrin complexes are generally useful for most dosage forms and administration routes. As an alternative to direct complexation with the protein or polypeptide, the cyclodextrin may be used as an auxiliary additive, e.g. as a carrier, diluent or solubiliser. Alpha-, beta- and gamma-cyclodextrins are most commonly used and suitable examples are described in published international patent applications WO91/11172, WO94/02518 and WO98/55148.

In some embodiments, pharmaceutical compositions of the present invention are provided in unit dosage form, such as tablets or capsules. It may be advantageous to formulate oral or parenteral compositions in unit dosage form for ease of administration and uniformity of dosage. In such form, the composition is sub-divided in unit dose containing appropriate quantities of the polypeptide or protein. The unit dosage forms can be packaged compositions, for example packeted powders, vials, ampoules, pre-filled syringes or sachets containing liquids. The unit dosage form can be, for example, a capsule or tablet itself, or it can be an appropriate number of any such compositions in package form. As one skilled in the art will recognize, therapeutically effective unit dosage will depend on several factors, including, for example, the method of administration, the potency of the polypeptide or protein, and/or the weight of the recipient and the identities of other components in the pharmaceutical composition.

A polypeptide or protein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a polypeptide or protein as described herein may comprise a single treatment or a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention encompasses the use of inventive compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8th edition, Iowa State University Press; ISBN: 0813817439; 2001.

Inventive pharmaceutical compositions can be included in a container, pack, or dispenser together with instructions for administration.

EXAMPLES

Example 1

Effect of 2-Deoxyglucose on Cell Growth of α-GDF-8 Cells in Culture Dishes

Introduction: Lactate is a known inhibitor of cell growth in cell culture (see Lao and Toth, *Biotechnology. Prog.* 13(5): 688-691, 1997). Decreasing the amount of glucose in cell culture leads to a concomitant decrease in the amount of lactate produced. 2-deoxyglucose is a structural analog of glucose in which the hydroxyl group at the 2' position of the sugar is replaced with a hydrogen moiety. Roth et al. have demonstrated that 2-deoxyglucose reduces glucose/energy flux when fed to rats without decreasing their total food intake (*Annals of the New York Academy of Sciences*, 928:305-15, 2001). In this example, experiments were performed to determine whether the addition of 2-deoxyglucose to mammalian cell culture was detrimental to the growth of the cells in culture dishes.

Materials and Methods: Chinese Hamster Ovary ("CHO") cells engineered to express a monoclonal antibody against growth and differentiation factor 8 ("α-GDF-8 cells") (see Veldman et al., Neutralizing Antibodies Against GDF-8 and Uses Therefor, US20040142382 A1) were grown in culture dishes in Medium 1 supplemented with glucose to a final initial concentration of 9 g/L with varying concentrations of 2-deoxyglucose. Table 1 shows the composition of Medium 1.

TABLE 1

| Composition of Medium 1. | | |
|---|---|---|
| Amino Acids | mg/L | mM |
| alanine | 17.80 | 0.20 |
| arginine | 347.97 | 2.00 |
| asparagine•H$_2$O | 75.00 | 0.50 |
| aspartic acid | 26.20 | 0.20 |
| cysteine•HCl•H$_2$O | 70.19 | 0.40 |
| cysteine•2HCl | 62.25 | 0.20 |
| glutamic acid | 29.40 | 0.20 |
| monosodium glutamate | 1163.95 | 7.98 |
| glutamine | | |
| glycine | 29.00 | 0.40 |
| histidine•HCl•H$_2$O | 46.00 | 0.22 |
| isoleucine | 105.00 | 0.80 |
| leucine | 105.00 | 0.80 |
| lysine•HCl | 145.99 | 0.80 |
| methionine | 29.80 | 0.20 |
| phenylalanine | 65.99 | 0.40 |
| proline | 68.99 | 0.60 |
| serine | 126.00 | 1.20 |
| threonine | 95.00 | 0.80 |
| tryptophan | 16.00 | 0.08 |
| tyrosine•2Na•2H$_2$O | 103.80 | 0.40 |
| valine | 93.99 | 0.80 |

TABLE 1-continued

Composition of Medium 1.

| Vitamins | mg/L | μM |
|---|---|---|
| biotin | 0.20 | 0.82 |
| calcium pantothenate | 2.24 | 4.71 |
| choline chloride | 8.98 | 64.60 |
| folic acid | 2.65 | 6.01 |
| inositol | 12.60 | 69.99 |
| nicotinamide | 2.02 | 16.56 |
| pyridoxal•HCl | 2.00 | 9.85 |
| pyridoxine•HCl | 0.03 | 0.15 |
| riboflavin | 0.22 | 0.59 |
| thiamine•HCl | 2.17 | 6.44 |
| vitamin B12 | 0.78 | 0.58 |
| Inorganic Salts | mg/L | mM |
| $CaCl_2$ | 116.09 | 1.05 |
| KCl | 311.77 | 4.18 |
| $Na_2HPO_4$ | 0.00 | 0.00 |
| NaCl | 70.99 | 0.50 |
| $NaH_2PO_4 \cdot H_2O$ | 5539 | 94.85 |
| $MgSO_4$ | 62.49 | 0.45 |
| $MgSO_4 \cdot 7H_2O$ | 48.83 | 0.41 |
| $MgCl_2$ | 0.00 | 0.00 |
| $NaHCO_3$ | 28.61 | 0.30 |
| Trace Elements | μg/L | nM |
| Sodium Selenite | 5.00 | 28.92 |
| $Fe(NO_3)_3 \cdot 9H_2O$ | 50.00 | 123.75 |
| $CuSO_4$ | 0.80 | 5.00 |
| $CuSO_4 \cdot 5H_2O$ | 0.00 | 0.00 |
| $FeSO_4 \cdot 7H_2O$ | 839.96 | 3021 |
| $ZnSO_4 \cdot 7H_2O$ | 429.96 | 1498 |
| Other Components | mg/L | μM |
| Hydrocortisone | 0.04 | 0.10 |
| Putrescine•2HCl | 1.08 | 6.70 |
| linoleic acid | 0.04 | 0.14 |
| thioctic acid | 0.10 | 0.49 |
| D-glucose (Dextrose) | 6150 | 34170 |
| PVA | 2400 | |
| Nucellin | 10.00 | |
| Sodium Pyruvate | 55.00 | 499.95 |

Results and Conclusion: The specific growth rates of the α-GDF-8 cells in cell culture dishes are shown in FIG. 1. The cells grown in the absence of 2-deoxyglucose exhibited a specific growth rate ("μ") of approximately 0.03 1/h. The addition of increasing amounts of 2-deoxyglucose reduced the specific growth rate in a dose-dependent manner. For example, cells grown in the presence of 1 g/L 2-deoxyglucose (a 2-deoxyglucose:glucose ratio of 1:9) exhibited a specific growth rate of just over 0.02 1/h while cells grown in the presence of 2.5 g/L 2-deoxyglucose exhibited a specific growth rate of approximately 0.015 1/h, roughly half that of cells grown in the absence of 2-deoxyglucose. Thus, it appears that the presence of 2-deoxyglucose inhibits cell growth and that a 2-deoxyglucose to glucose ratio greater than approximately 1 to 9 reduces the specific growth rate to a level below half that observed in the absence of 2-deoxyglucose.

Example 2

Effect of 2-Deoxyglucose on Lactate of α-GDF-8 Cells in Culture Dishes

Introduction: Example 1 demonstrated that cell cultures grown in culture dishes tolerated 2-deoxyglucose well when provided at low concentrations. In this example, experiments were performed to test whether the presence of 2-deoxyglucose had an effect on the accumulation of lactate in cell cultures grown in culture dishes.

Materials and Methods: α-GDF-8 cells were grown in culture dishes in Medium 1 containing approximately 6 g/L glucose with varying concentrations of 2-deoxyglucose. Some α-GDF-8 cultures were optionally supplemented with glucose to a final initial concentration of 9 g/L. Cells were passaged twice and grown for three days after each passage. At the end of three days, each of the passaged cultures was measured for viability, cell density, glucose levels, lactate levels and α-GDF-8 titer. Specific titer production rate ("Qp") and specific lactate uptake rate ("Qlact") were calculated. Qlact was calculated as follows: ((final lactate level−initial lactate level)/(final cell density−initial cell density))×growth rate×24, where lactate levels are measured in g/L, cell densities are measured in $10^6$ cells/ml, growth rate is measured as 1/h, and the final Qlact is calculated as mg/e6/day. Qp was calculated as follows: ((final titer−initial titer)/(final cell density−initial cell density))×growth rate×24, where titer is measured in mg/L, cell density is measured in $10^6$ cells/ml, growth rate is measured as 1/h, and Qp is calculated as μg/e6/day.

Results: Table 2 shows the starting and final cell densities, viability, final glucose and lactate concentrations, specific growth rate, titer, Qlact and Qp of the two passaged α-GDF-8 cell cultures. As can be seen, the viability of the cells is largely unaffected by the presence of 2-deoxyglucose in the cell culture, at least up to a ratio of 2-deoxyglucose to glucose of 1 to 6 (Table 2, column labeled "viab"). However, the specific growth rate of the cells is negatively affected by the presence of 2-deoxyglucose in a dose-dependent manner (Table 2, columns labeled "μ"). The control cultures of the first and second passages exhibit a specific growth rate of 0.032 and 0.037, respectively while the cultures grown in the presence of 1 g/L 2-deoxyglucose exhibit specific growth rates of 0.027 (first passage, 9 g/L glucose), 0.028 (second passage, 9 g/L glucose) and 0.027 (second passage, 6 g/L glucose). Thus, similar to the results seen in Example 1, the presence of 2-deoxyglucose in the cell culture inhibits the specific growth rate.

The presence of 2-deoxyglucose in the cell culture also reduced the accumulation of lactate in the culture in a dose-dependent manner. As shown in Table 2 (column labeled "lact"), in the first passage, lactate accumulated in the control culture lacking 2-deoxyglucose to a level of 1.88 g/L, while in the presence of 1 g/L 2-deoxyglucose (with 9 g/L glucose), lactate only accumulated to a level of 0.9 g/L. Similarly, in the second passage, lactate accumulated in the control culture lacking 2-deoxyglucose to a level of 2.39 g/L, while in the presence of 1 g/L 2-deoxyglucose, lactate only accumulated to a level of 0.98 g/L (with 9 g/L glucose) or 0.68 g/L (with 6 g/L glucose). Furthermore, as can be seen in Table 2, not only did the total lactate decrease in cell culture as the ratio of 2-deoxyglucose to glucose increased, but the specific lactate production rate ("Qlact") also decreased. In the first passage, the control culture containing no 2-deoxyglucose had a Qlact of 0.948, while in a culture containing a one to nine ratio of 2-deoxyglucose to glucose, the Qlact fell to 0.553. Similarly, in the second passage, the control culture containing no 2-deoxyglucose had a Qlact of 0.582, while in a culture containing a one to nine ratio of 2-deoxyglucose to glucose, the Qlact fell to 0.290.

The presence of 2-deoxyglucose in the cell culture also reduced the α-GDF-8 titer in a dose-dependent manner. As shown in Table 2 (column labeled "titer"), in the second passage, α-GDF-8 accumulated in the control culture lacking 2-deoxyglucose to a level of 67.3 mg/L, while in the presence of 1 g/L 2-deoxyglucose (with 6 g/L glucose), α-GDF-8 only accumulated to a level of 28.22 mg/L. Furthermore, as can be seen in Table 2, not only did the total titer decrease in cell culture as the ratio of 2-deoxyglucose to glucose increased, but the specific titer production rate ("Qp") also decreased. In the second passage, the control culture containing no 2-deoxyglucose had a Qp of 16.376 while in a culture containing a one to six ratio of 2-deoxyglucose to glucose, the Qp fell to 12.038.

Materials and Methods: α-GDF-8 cells were grown in Medium 2 in 1 L Bioreactors and fed with Medium 3. The compositions of Medium 2 and Medium 3 are shown in Table 3. Some of the cultures were supplemented with 0.5 g/L 2-deoxyglucose at the beginning of the culture. The cultures were shifted from 37° Celsius to 31° Celsius on either day 4 ("early shift") or day 6 ("late shift"). The experimental conditions and feeding schedule for cell cultures grown in Bioreactors is summarized in Table 4.

TABLE 2

Effect of 2-Deoxyglucose on Lactate of α-GDF-8 Cells in Culture Dishes

First passage

| Conditions | c.d (start) | c.d (end) | viab | Gluc | lact | μ | Qlact |
|---|---|---|---|---|---|---|---|
| Control | 0.16 | 1.54 | 99.4 | 6.86 | 1.88 | 0.032 | 0.948 |
| 0.25/9 | 0.14 | 1.3 | 99.7 | 7.55 | 1.53 | 0.032 | 0.899 |
| 0.5/9 | 0.16 | 1.12 | 99.3 | 7.88 | 1.22 | 0.028 | 0.727 |
| 0.5/6 | 0.15 | 1.24 | 99.1 | 5.21 | 1.2 | 0.030 | 0.701 |
| 1/9. | 0.16 | 1.05 | 99.7 | 8.13 | 0.9 | 0.027 | 0.553 |
| 1/6. | | | | | | | |

Second passage

| Conditions | c.d (start) | c.d (end) | viab | Gluc | lact | titer | Qp | Qlact | μ |
|---|---|---|---|---|---|---|---|---|---|
| Control | 0.26 | 3.6 | 99.1 | 6.97 | 2.39 | 67.3 | 16.376 | 0.582 | 0.037 |
| 0.25/9 | 0.25 | 3.2 | 99.5 | 7.25 | 2.17 | 58.28 | 15.477 | 0.576 | 0.035 |
| 0.5/9 | 0.26 | 2.8 | 99.6 | 7.65 | 1.79 | 50.37 | 14.252 | 0.506 | 0.033 |
| 0.5/6 | 0.24 | 2.6 | 99 | 5.04 | 1.36 | 43 | 13.135 | 0.415 | 0.033 |
| 1/9. | 0.25 | 1.9 | 99 | 9 | 0.98 | 34.85 | 12.400 | 0.349 | 0.028 |
| 1/6. | 0.22 | 1.5 | 98.6 | 6.51 | 0.68 | 28.22 | 12.038 | 0.290 | 0.027 |

Note:
Numbers in the first column indicate the ratio of g/L deoxyglucose to g/L glucose. Thus, 0.25/9 indicates 0.25 g/L deoxyglucose and 9 g/L glucose Conclusion: Similar to the results seen in Example 1, the presence of 2-deoxyglucose in the cell culture inhibited cell growth in a dose-dependent manner. As a result, the final cell density was lower in cultures supplemented with 2-deoxyglucose and the titer of expressed α-GDF-8 was decreased in a manner directly proportional to the ratio of 2-deoxyglucose to glucose in the culture. However, the presence of 2-deoxyglucose appeared to have little or no effect on the viability of cells in the cell culture. Importantly, the presence of 2-deoxyglucose in the cell culture inhibited accumulation of lactate in a dose-dependent manner. Since lactate is a known inhibitor of cell growth and viability at high cell densities, these results demonstrate that the addition of 2-deoxyglucose to a cell culture may result in a higher final cell density or a healthier cell culture at higher cell densities.

Example 3

Effect of 2-Deoxyglucose on Cell Growth and Productivity of α-GDF-8 Cells in Bioreactors Introduction: Examples 1 and 2 demonstrated that cell cultures grown in culture dishes tolerated added 2-deoxyglucose well when provided at low concentrations and that lactate accumulation was decreased in the presence of 2-deoxyglucose. In this example, experiments were performed to determine whether 2-deoxyglucose decreased the amount of lactate produced during cell cultures grown in Bioreactors and whether the presence of 2-deoxyglucose had other beneficial or detrimental effects aside from the reduction in growth rate, particularly as the cell culture is grown for an extended period of time.

TABLE 3

Composition of Medium 2 and Medium 3.

| | Medium 2 | | Medium 3 | |
|---|---|---|---|---|
| Amino Acids | mg/L | mM | mg/L | mM |
| alanine | 17.80 | 0.20 | 213.68 | 2.40 |
| arginine | 696.00 | 4.00 | 2292 | 13.18 |
| asparagine•H$_2$O | 3000 | 20.00 | 3240 | 21.60 |
| aspartic acid | 219.45 | 1.65 | 799.98 | 6.01 |
| cysteine•HCl•H$_2$O | 70.40 | 0.40 | | |
| cysteine•2HCl | 468.75 | 1.50 | 586 | 1.87 |
| glutamic acid | | | 353.67 | 2.41 |
| monosodium glutamate | 33.80 | 0.20 | | |
| glutamine | 584.00 | 4.00 | | |
| glycine | 115.50 | 1.54 | 180.07 | 2.40 |
| histidine•HCl•H$_2$O | 474.60 | 2.26 | 882.35 | 4.20 |
| isoleucine | 570.73 | 4.36 | 1416 | 10.81 |
| leucine | 1030 | 7.87 | 2040 | 15.58 |
| lysine•HCl | 1401 | 7.70 | 2184 | 12.00 |
| methionine | 387.40 | 2.60 | 715.48 | 4.80 |
| phenylalanine | 507.00 | 3.07 | 990.39 | 6.00 |
| proline | 539.50 | 4.69 | 828.32 | 7.20 |
| serine | 1052 | 10.02 | 1896 | 18.06 |
| threonine | 564.80 | 4.75 | 1142 | 9.60 |
| tryptophan | 274.16 | 1.34 | 391.325 | 1.92 |
| tyrosine•2Na•2H$_2$O | 745.75 | 2.86 | 1251 | 4.79 |
| valine | 749.00 | 6.40 | 1123 | 9.60 |
| Vitamins | mg/L | μM | mg/L | μM |
| biotin | 2.68 | 11.00 | 4.92 | 20.17 |
| calcium pantothenate | 21.92 | 46.06 | 54.02 | 113.49 |
| choline chloride | 158.46 | 1140. | 214.88 | 1545 |
| folic acid | 25.93 | 58.80 | 63.76 | 144.57 |

TABLE 3-continued

Composition of Medium 2 and Medium 3.

| inositol | 163.98 | 911.00 | 302.52 | 1680 |
|---|---|---|---|---|
| nicotinamide | 26.23 | 215.00 | 48.02 | 393.60 |
| pyridoxal•HCl | 2.03 | 10.00 | | |
| pyridoxine•HCl | 36.13 | 175.38 | 49.22 | 238.93 |
| riboflavin | 2.41 | 6.42 | 5.40 | 14.37 |
| thiamine•HCl | 39.43 | 117.00 | 92.82 | 275.43 |
| vitamin B12 | 21.17 | 15.62 | 16.81 | 12.40 |

| Inorganic Salts | mg/L | mM | mg/L | mM |
|---|---|---|---|---|
| $CaCl_2$ | 116.55 | 1.05 | | |
| KCl | 312.90 | 4.19 | | |
| $Na_2HPO_4$ | 56.60 | 0.40 | | |
| NaCl | 1100 | 18.80 | | |
| $NaH_2PO_4 \cdot H_2O$ | 645.84 | 4.68 | 1566.00 | 11.40 |
| $MgSO_4$ | | | | |
| $MgSO_4 \cdot 7H_2O$ | 138.00 | 1.15 | 258.00 | 1.05 |
| $MgCl_2$ | 28.50 | 0.30 | | |
| $NaHCO_3$ | 2000 | 23.81 | | |

| Trace Elements | µg/L | nM | µg/L | nM |
|---|---|---|---|---|
| Sodium Selenite | 69.16 | 400.00 | 60.00 | 347.02 |
| $Fe(NO_3)_3 \cdot 9H_2O$ | 50.00 | 123.76 | | |
| $CuSO_4$ | 10.24 | 64.00 | | |
| $CuSO_4 \cdot 5H_2O$ | 99.88 | 400.00 | 5.16 | 32.26 |
| $FeSO_4 \cdot 7H_2O$ | 4170 | 15000 | 18.54 | 74.24 |
| $ZnSO_4 \cdot 7H_2O$ | 2640 | 9200 | 6859 | 24675 |
| $MnSO_4 \cdot H_2O$ | 33.80 | 200.00 | 4897 | 17062 |
| $Na_2SiO_3 \cdot 9H_2O$ | 284.07 | 1000 | 1.15 | 6.79 |
| $(NH4)_6Mo_7O_{24} \cdot 4H_2O$ | 247.20 | 200.00 | 945.00 | 3326 |
| $NH_4VO_3$ | 2.34 | 20.00 | 8.37 | 6.77 |
| $NiSO_4 \cdot 6H_2O$ | 5.26 | 20.00 | 4.39 | 37.50 |
| $SnCl_2 \cdot 2H_2O$ | 0.90 | 4.00 | 0.88 | 3.34 |
| $AlCl_3 \cdot 6H_2O$ | 0.97 | 4.00 | | |
| KBr | 0.48 | 4.00 | | |
| $CrCl_3$ | 15.83 | 100.00 | | |
| NaF | 0.17 | 4.00 | | |
| $GeO_2$ | 0.42 | 4.00 | | |
| KI | 33.20 | 200.00 | | |
| RbCl | 0.48 | 4.00 | | |
| $H_3BO_3$ | 12.37 | 200.00 | | |
| LiCl | 0.17 | 4.00 | | |

| Other Components | mg/L | µM | mg/L | µM |
|---|---|---|---|---|
| Hydrocortisone | 540.00 | 1.49 | 0.43 | 1.19 |
| Putrescine•2HCl | 15000 | 93.11 | 12.00 | 74.49 |
| linoleic acid | 290.00 | 1.04 | 0.51 | 1.80 |
| thioctic acid | 716.00 | 3.48 | 1.26 | 6.13 |
| D-glucose (Dextrose) | 15000 | 83.33 | 50329 | 279609 |
| PVA | 2560 | | 2400 | |
| Nucellin | 50.00 | | 120.00 | |
| Sodium Pyruvate | 55.00 | 0.50 | | | described in Table 4. As can be seen in FIG. 2, the cell density of the late shifted cells grown in the presence of 2-deoxyglucose was significantly higher beginning on approximately day 4 than any of the other three conditions. Furthermore, the viability of late shifted cells grown in the presence of 2-deoxyglucose was significantly higher than the viability of late shifted cells grown in the absence of 2-deoxyglucose. A comparison of FIGS. 4 and 5 shows that the overall titer of α-GDF-8 is inversely correlated with the amount of lactate in the culture. The two early shifted cultures (containing and lacking 2-deoxyglucose) each had the lowest levels of lactate by the end of the culture and each had the highest overall titers. We note that the early shifted culture that contained 2-deoxyglucose had slightly lower lactate levels than the early shifted culture that lacked 2-deoxyglucose and had a correspondingly slightly higher final titer. Similarly, the late shifted culture that contained 2-deoxyglucose had slightly lower lactate levels than the late shifted culture that lacked 2-deoxyglucose and had a correspondingly slightly higher final titer. Both of the early shifted cultures showed a reduction in lactate levels beginning on approximately day 4, the day of the temperature shift. However, both of the late shifted cultures failed to show a reduction in lactate levels after the shift and lactate levels continued to increase throughout the life of the culture.

Conclusions: In contrast to the detrimental effect on cell density seen in cell cultures grown for only a few days in culture dishes in Examples 1 and 2, this example demonstrated that the presence of 2-deoxyglucose in a cell culture grown in a Bioreactor for 12 days resulted in a significantly higher cell density at the end of the culture than either cell cultures grown in the absence of 2-deoxyglucose or a cell culture grown with 2-deoxyglucose but temperature shifted two days earlier. Additionally, a late shifted culture that contained 2-deoxyglucose exhibited a significantly higher viability than a late shifted culture that lacked 2-deoxyglucose. Furthermore, cell cultures grown in media with 2-deoxyglucose contained lower resulting lactate levels than corresponding cultures grown in media that lacked 2-deoxyglucose. Significantly however, both early shifted cultures exhibited a reduction in overall lactate levels after the temperature shift, while both late shifted cultures continued to accumulate lactate throughout the course of the culture. The lactate levels at the time of the shift of the early cultures were well below the lactate levels at the time of the shift of the late shifted cultures. Thus, it is possible that lactate levels at the time of the shift determine whether cells in a culture will begin to take up lactate. However, although the lactate level of the late shifted

TABLE 4

Bioreactor conditions for Example 3.

| Condition | 2-deoxyglucose | Temp shift | Feed Day 5 | Day 6 | Day 7 | Day 10 | Day 11 |
|---|---|---|---|---|---|---|---|
| 1 | — | Day 4 | | | 5% by volume | 3 g/L glucose | 2 g/L glucose |
| 2 | 0.5 g/L | Day 4 | | | 5% by volume | 3 g/L glucose | 2 g/L glucose |
| 3 | — | Day 6 | 10% by volume, 2.5 g/L glucose | 5 g/L glucose | 5% by volume | 3 g/L glucose | |
| 4 | 0.5 g/L | Day 6 | 10% by volume, 2.5 g/L 2-deoxyglucose | 5 g/L glucose | 5% by volume, .025 g/L 2-deoxyglucose | 3 g/L glucose | 2 g/L glucose |

Results: FIGS. 2, 3, 4 and 5 show the daily cell density, viability, lactate concentration and titer of α-GDF-8 cells grown in production Bioreactors under the four conditions culture that lacked 2-deoxyglucose was significantly higher at the time of the shift than the lactate levels at the time of the shift of the two early shifted cultures (see FIG. 4, approximately 10 g/L vs. approximately 4-5 g/L), the lactate level of the late shifted culture that contained 2-deoxyglucose was not significantly higher (see FIG. 4, approximately 6 g/L vs. approximately 4-5 g/L). However, the cell density of the late shifted, 2-deoxyglucose containing culture was significantly higher (see FIG. 2, approximately $18 \times e^6$/mL vs. $12 \times e^6$/mL). Thus, in addition to the lactate level at the time of the shift, this example demonstrates that cell density at the time of the shift may also play a role in determining whether cells in a culture will begin to take up lactate.

Finally, this Example demonstrates that the titer of a culture is inversely correlated to the levels of lactate in the culture. Thus, the early shifted cultures that began to take up lactate had the highest final titers, while the late shifted cultures that continued to accumulate lactate had the lowest final titers. This is so even though the late shifted culture containing 2-deoxyglucose had a significantly higher cell density. It thus appears that excess lactate levels affect the productivity of the late-shifted cells grown in a medium containing 2-deoxyglucose.

Example 4

Effect of 2-Deoxyglucose on Cell Growth and Productivity of α-GDF-8 Cells in Bioreactors Introduction: Example 3 demonstrated that the presence of 2-deoxyglucose in a cell culture grown in a Bioreactor for 12 days resulted in a significantly higher cell density at the end of the culture than either cell cultures grown in the absence of 2-deoxyglucose or a cell culture grown with 2-deoxyglucose but temperature shifted two days earlier. Additionally, 2-deoxyglucose containing cultures accumulated lactate to a lesser extent than corresponding cultures that lack 2-deoxyglucose. However, due to the high lactate levels and/or the high cell densities at the time of the shift, titer of the late shifted cultures was significantly reduced. In this Example, we attempt to restore the titer of late shifted cultures by altering the lactate levels and/or cell densities at the time of the shift.

Materials and Methods: α-GDF-8 cells were grown in Medium 2 in 1 L Bioreactors and fed with Medium 3. Some of the cultures were supplemented with 0.5 g/L 2-deoxyglucose at the beginning of the culture. The cells were fed with either 3 g/L glucose or 0.3 g/L 2-deoxyglucose on day 4 and with either 10% feed medium (by volume) or 10% feed medium (by volume) supplemented with 0.2 g/L 2-deoxyglucose on day 5. The cultures were shifted from 37° Celsius to 31° Celsius on either day 5 ("early shift") or day 6 ("late shift"). Additional feeds were provided on days 7 and 10. The experimental conditions for cell cultures grown in Bioreactors are summarized in Table 5.

TABLE 5

Bioreactor conditions for Example 4.

| RXT # | 2-deoxyglucose | Temp shift | Feed Day 4 | Day 5 | Day 7 | Day 10 |
|---|---|---|---|---|---|---|
| 1 | — | Day 6 | 3 g/L glucose | 10% by volume | 5% by volume | 2.5 g/L glucose |
| 2 | — | Day 5 | 3 g/L glucose | 10% by volume | 5% by volume | 2.5 g/L glucose |
| 3 | 0.5 g/L | Day 5 | 0.3 g/L 2-deoxyglucose | 10% by volume, with 0.2 g/L 2-deoxyglucose | 5% by volume | 2.5 g/L glucose |
| 4 | 0.5 g/L | Day 6 | 0.3 g/L 2-deoxyglucose | 10% by volume with 0.2 g/L 2-deoxyglucose | 10% by volume | 2.5 g/L glucose |

Results: FIGS. 6, 7 and 8 show the daily cell density, lactate concentration and titer of α-GDF-8 cells grown in production Bioreactors under the four conditions described in Table 5. Similar to the result seen in Example 3, FIG. 6 shows that the cell density of the late shifted cells grown in the presence of 2-deoxyglucose is significantly higher beginning on approximately day 5 than any of the other three conditions. FIG. 7 shows that all cell cultures underwent a reduction in lactate levels after being shifted to a lower temperature. Additionally, the cell culture containing 2-deoxyglucose that was shifted late had a lower final lactate concentration than cell cultures that were shifted early, regardless of whether 2-deoxyglucose was present. Furthermore, overall lactate levels were similar between late shifted cell cultures either grown in the presence or absence of 2-deoxyglucose. However, since FIG. 6 shows that the late shifted cell culture grown in the presence of 2-deoxyglucose contained more cells, it follows that the cells in the 2-deoxyglucose culture either produced less lactate than cells grown in the absence of 2-deoxyglucose, or in some way metabolized existing lactate to a greater extent than cells grown in the absence of 2-deoxyglucose or both. FIG. 8 shows that the overall titer of α-GDF-8 was similar for all four culture conditions. However, since the overall cell density of the late shifted cells grown in the presence of 2-deoxyglucose was higher (see FIG. 6), the late shifted 2-deoxyglucose cells appear to have produced less α-GDF-8 per cell than cells grown under the other three culture conditions.

FIG. 9 shows the glucose uptake of α-GDF-8 cells grown under the four conditions described in Table 5. The presence of 2-deoxyglucose in the culture medium resulted in a decrease in the glucose uptake (FIG. 9, $3^{rd}$ and $4^{th}$ bars). Additionally, the late shifted cells grown in the presence of 2-deoxyglucose took up glucose at a lower rate than early shifted cells grown in the presence of 2-deoxyglucose.

Conclusion: Similar to the results seen in Example 3, this example demonstrates that the presence of 2-deoxyglucose in a cell culture grown in a Bioreactor for 12 days resulted in a significantly higher cell density at the end of the culture than either cell cultures grown in the absence of 2-deoxyglucose or a cell culture grown with 2-deoxyglucose but temperature shifted one day earlier. Significantly, it appears that the cells grown in the presence of 2-deoxyglucose produced less lactate and/or consumed lactate to a greater extent than cells grown in the absence of 2-deoxyglucose (compare the cell densities of the two samples as shown in FIG. 6 to the overall lactate accumulation shown in FIG. 7). It should also be noted that the late shifted cell culture grown in the presence of 2-deoxyglucose contained lower overall lactate levels than early shifted cell cultures grown either in the presence or absence of 2-deoxyglucose. Finally, although the amount of α-GDF-8 produced per cell is lower in late shifted 2-deoxyglucose cultures (compare the cell densities of the two samples as shown in FIG. 6 to the overall α-GDF-8 titer shown in FIG. 8), the overall α-GDF-8 titer is similar to the α-GDF-8 titer of cell cultures grown in the absence of 2-deoxyglucose, demonstrating that the presence of 2-deoxyglucose has a positive effect on overall cell density but, in contrast to the results of Example 3, does not have a detrimental effect on final α-GDF-8 titer. Thus, the present invention demonstrates that by manipulating culture conditions such that lactate is taken up after the temperature shift, it is possible to increase cell density of the late shifted culture containing 2-deoxyglucose without a corresponding negative effect on overall α-GDF-8 titer.

Example 5

Effect of 2-Deoxyglucose on Cell Growth and Productivity of α-GDF-8 Cells in Bioreactors in the Presence of High Glucose Introduction: Example 4 demonstrated that the presence of 2-deoxyglucose in production Bioreactors resulted in an increased overall cell density at the end of 12 days when the cells were temperature shifted late. Although overall α-GDF-8 titer was similar to the α-GDF-8 titer of cell cultures grown in the absence of 2-deoxyglucose, α-GDF-8 production per cell was significantly lower. In this example, experiments were performed to determine whether α-GDF-8 production per cell could be increased by supplementing the culture periodically with additional glucose.

Materials and Methods: α-GDF-8 cells were grown in Medium 2 in 1 L Bioreactors and fed with Medium 3. The starting culture media were either supplemented or not with 0.5 g/L 2-deoxyglucose. The cells were fed on days 3, 5, 7, 10 and 12 to keep the glucose level at above approximately 8 g/L. The cultures lacking 2-deoxyglucose were shifted from 37° Celsius to 31° Celsius on day 4, while the cultures containing 2-deoxyglucose were shifted from 37° Celsius to 31° Celsius on day 5.

Results: FIGS. 10, 11, 12, 13 and 14 show daily viable cell density, titer, lactate, glucose levels and specific cellular productivity respectively for α-GDF-8 cells grown either in the presence or absence of 2-deoxyglucose. As shown in FIG. 10, the cell densities of the two cultures are similar at the beginning and the end of the culture, although the cell density of the culture supplemented with 2-deoxyglucose was slightly higher during the middle stage of the culture. FIG. 11 shows that the overall α-GDF-8 titer is also similar between the two cultures, although the α-GDF-8 titer of the culture supplemented with 2-deoxyglucose is slightly higher by day 14. Thus, in the presence of high levels of glucose, the decrease in the titer per cell seen in Examples 3 and 4 appears to have been eliminated. The similarity between the α-GDF-8 production of cell cultures either containing or lacking 2-deoxyglucose is also indicated in FIG. 14, which shows the daily specific cellular productivity of α-GDF-8. Consistent with the data presented in the previous three examples, FIG. 12 shows that lactate accumulation in cell cultures containing 2-deoxyglucose is significantly lower than in cell cultures lacking 2-deoxyglucose. FIG. 13 shows the glucose levels each day over the course of the cultures. The sharp increases on days 3, 5, 7, 10 and 12 correspond to addition of feed media.

Conclusions: This example demonstrates that in the presence of high levels of glucose, the reduction in amount of α-GDF-8 produced per cell in the presence of 2-deoxyglucose seen in Examples 4 and 5 is eliminated. Additionally, even in the presence of high glucose levels, the beneficial reduction of lactate in the culture medium resulting from the presence of 2-deoxyglucose persists. Thus, the cells grown in the presence of 2-deoxyglucose were able to be temperature shifted one day later, resulting in a higher overall integrated viable cell density than cells grown in the absence of 2-deoxyglucose.

The invention claimed is:

1. A cell culture medium comprising 2-deoxyglucose and glucose, wherein the ratio of the 2-deoxyglucose to glucose is equal to or less than about 1 to 9, and wherein the cell culture medium does not contain serum.

2. The medium of claim 1, wherein 2-deoxyglucose is present at between approximately 0.25 grams per liter and 1 gram per liter.

3. The medium of claim 1, further comprising glutamine at less than 13 mM.

4. The medium of claim 1, wherein the medium comprises glucose at 8 g/L or above.

5. The medium of claim 1, wherein the cell culture medium has a medium characteristic selected from the group consisting of: (i) a cumulative amino acid concentration greater than about 70 mM, (ii) a molar cumulative glutamine to cumulative asparagine ratio of less than about 2, (iii) a molar cumulative glutamine to cumulative total amino acid ratio of less than about 0.2, (iv) a molar cumulative inorganic ion to cumulative total amino acid ratio between about 0.4 to 1, (v) a combined cumulative glutamine and cumulative asparagine concentration between about 16 and 36 mM, and combinations thereof.

6. The medium of claim 1, further comprising manganese at a concentration between approximately 10 and 600 nM.

7. The medium of claim 1, wherein the medium is defined.

* * * * *